US012714336B2

(12) United States Patent
Kovatchev et al.

(10) Patent No.: US 12,714,336 B2
(45) Date of Patent: Aug. 25, 2026

(54) METHOD AND SYSTEM FOR MODEL-BASED TRACKING OF HEMOGLOBIN A1c FROM DAILY CONTINUOUS GLUCOSE MONITORING PROFILES

(71) Applicant: University of Virginia Patent Foundation, Charlottesville, VA (US)

(72) Inventors: Boris P. Kovatchev, Charlottesville, VA (US); Chiara Fabris, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 1006 days.

(21) Appl. No.: 17/776,717

(22) PCT Filed: Nov. 16, 2020

(86) PCT No.: PCT/US2020/060658
§ 371 (c)(1),
(2) Date: May 13, 2022

(87) PCT Pub. No.: WO2021/097396
PCT Pub. Date: May 20, 2021

(65) Prior Publication Data

US 2022/0395200 A1 Dec. 15, 2022

Related U.S. Application Data

(60) Provisional application No. 62/935,408, filed on Nov. 14, 2019.

(51) Int. Cl.

*A61B 5/145* (2006.01)
*A61M 5/172* (2006.01)
*G16H 50/20* (2018.01)

(52) U.S. Cl.
CPC ......... *A61B 5/14532* (2013.01); *G16H 50/20* (2018.01); *A61M 5/1723* (2013.01)

(58) Field of Classification Search
CPC .............. A61B 5/14532; A61B 5/7267; A61B 5/00–7495; G16H 50/20; G16H 20/17;
(Continued)

(56) References Cited

U.S. PATENT DOCUMENTS

2013/0079613 A1 3/2013 Kovatchev et al.
2018/0235524 A1 8/2018 Dunn et al.
(Continued)

OTHER PUBLICATIONS

Kovatchev, Boris p et al., Accuracy and Robustness of Dynamical Tracking of Average Glycemia (A1c) to Provide Real-Time Estimation of Hemoglobin A1c Using Routine Self-Monitored Blood Glucose Data, 2014, Diabetes Technology & Therapeutics, vol. 16, No. 5, pp. 303-309. (Year: 2014).*
(Continued)

*Primary Examiner* — Tse W Chen
*Assistant Examiner* — Evelyn Grace Park
(74) *Attorney, Agent, or Firm* — Potomac Law Group, PLLC; Brian H. Buck; Vincent M DeLuca

(57) ABSTRACT

A method, system, and computer-readable medium for providing a real-time estimation of laboratory glycosylated hemoglobin (HbA1c) at one or more intervals. The real-time estimation is conferred as a value of estimated, time variable A1e (eA1c) based on daily continuous glucose monitoring (CGM)-derived time in target range (TIR) (CGM-TIR). The eA1c value is adjusted based on a sole laboratory HbA1c value for an interval preceding an interval corresponding to the eA1c value so as to provide an expected value for a laboratory HbA1c value at the same corresponding interval.

18 Claims, 12 Drawing Sheets

(58) Field of Classification Search
CPC ........ G16H 40/63; G16H 40/67; G16H 50/50; G16H 50/70; A61M 5/1723; A61M 2230/201; A61H 2230/202
See application file for complete search history.

(56) References Cited

U.S. PATENT DOCUMENTS

| | | | | |
|---|---|---|---|---|
| 2018/0364262 | A1 | 12/2018 | Malka et al. | |
| 2019/0147139 | A1 * | 5/2019 | Roy | G16H 10/60 600/365 |
| 2019/0244690 | A1 | 8/2019 | Atkin | |
| 2019/0252055 | A1 | 8/2019 | Breton et al. | |
| 2021/0378561 | A1 * | 12/2021 | Xu | A61B 5/4836 |

OTHER PUBLICATIONS

Fabris et al; "Estimation of Hemoglobin A1c from Continuous Glucose Monitoring Data in Individuals with Type 1 Diabetes: Is Time In Range All We Need?"; vol. 22; No. 7; Jul. 1, 2020; pp. 501-508.

Kovatchev et al.; "Accuracy and Robustness of Dynamical Tracking of Average Glycemia (A1c) to Provide Real-Time Estimation of Hemoglobin A1c Using Routine Self-Monitored Blood Glucose Data"; vol. 16; No. 5; Apr. 23, 2014; pp. 303-309.

* cited by examiner

METHOD AND SYSTEM FOR MODEL-BASED TRACKING OF HEMOGLOBIN A1c FROM DAILY CONTINUOUS GLUCOSE MONITORING PROFILES

CROSS-REFERENCE TO RELATED APPLICATION

This international application claims priority to and the benefit of U.S. Provisional Application No. 62/935,408, filed Nov. 14, 2019, the entire contents which is incorporated by reference herein.

STATEMENT OF GOVERNMENT INTEREST

This invention was made with government support under Grant No. UC4 DK 108483 awarded by The U.S. National Institutes of Health and The National Institute of Diabetes and Digestive Kidney Diseases. The government has certain rights in the invention.

FIELD OF THE DISCLOSURE

Disclosed embodiments relate to estimation of laboratory glycosylated hemoglobin (HbA1c), and more specifically, to such estimation as enabled by deployment of an individualized dynamical model of hemoglobin glycation conferring estimated A1c sourced from daily continuous glucose monitoring (CGM)-derived time in target range (TIR) (CGM-TIR).

BACKGROUND

Type 1 diabetes mellitus (T1DM; herein T1D) is an autoimmune condition resulting in absolute insulin deficiency and a life-long need for exogenous insulin. Glycemic control in T1D remains a challenge, despite the availability of modern insulin analogues, and advanced technology such as insulin pumps, continuous glucose monitoring (CGM) and artificial pancreas (AP) systems that automatically titrate insulin doses.

HbA1c has been the gold-standard metric to assess quality of glycemic control in individuals with T1D since the landmark Diabetes Control and Complications Trial (DCCT) established that lowering HbA1c delays the onset and slows the progression of long-term diabetes complications.[1,2] Generally speaking, HbA1c is an indicator of average glycemia, reflecting blood glucose (BG) concentrations for the previous 2 to 3 months.[3] As such, HbA1c is driven mainly by hyperglycemia and is less related to acute hypoglycemic events or glycemic variability, which was in turn identified as an HbA1c-independent risk factor for the development of diabetes comorbidities.[4-6] Furthermore, because of individual differences in the rates of hemoglobin glycation and the lifespan of red blood cells:[7,8]the relationship between HbA1c and average glycemia varies among individuals and sub-populations.[9-14] Racial differences in the mean BG-HbA1c relationship are an example of the impact of such variability, with average HbA1c in non-Hispanic African American persons being about 0.4% higher than those of non-Hispanic white persons for a given CGM-derived mean glucose concentration.[15]

Since a wide range of mean glucose concentrations can be associated with the same HbA1c value, reflecting at least in part differences in individual glycation rates, the use of HbA1c as a sole metric to assess individual patients' glycemic control has been a matter of debate.[16-18] For example, Beck et al.[16] looked at data from 387 individuals with T1D and showed that central laboratory-measured HbA1c may substantially over- or underestimate CGM-derived mean BG, with an average 95% confidence interval of 63 mg/dL for a given HbA1c value. Moreover, HbA1c fails to reflect average glycemia in the presence of certain pathological conditions, such as hemoglobinopathies,[19] anemia,[20] and iron deficiency,[21] or in physiological states such as pregnancy.[22]

Owing to these possible discrepancies between HbA1c and average glycemic levels, mathematical models have been developed to estimate HbA1c from self-monitoring of BG or CGM measurements.[8,23-26] In 2018, Bergenstal and co-workers introduced a new metric for converting CGM-derived mean BG to HbA1c units, which was named "glucose management indicator" (GMI).[27,28] A decision was made to abandon the term "estimated A1c" (eA1c) to avoid confusion if eA1c and laboratory HbA1c did not agree. The formula to compute GMI was obtained by regressing central laboratory-measured HbA1c on CGM-derived average BG using a data set comprising 528 mean BG-HbA1c pairs. The authors reported that 19% of the GMI estimates differed by less than 0.1% from the reference HbA1c values, whereas 51% differed by 0.3% or more, reinforcing the need for a better understanding of the mismatches between GMI and laboratory HbA1c.

Using estimates of HbA1c obtained from the GMI computation or other linear transformations of average BG, it is possible to calculate the difference between estimated and measured HbA1c. This difference defines the hemoglobin glycation index (HGI),[29] a metric designed to quantify biological variations in HbA1c independent from average BG.[9,30] HGI is reported to differ between individuals and be consistent within individuals over time,[9,30,31] supporting the hypothesis that a patient-specific systematic bias in HbA1c exists that is likely sustained over time. Debate remains regarding the role of HGI as an independent risk factor for microvascular complications in T1D.[30,32] Interestingly, Hempe et al.[33] showed that intensive treatment with an HbA1c goal of less than 6% in individuals with type 2 diabetes was associated with improved cardiovascular outcomes in the low and moderate HGI subgroups, but not in the high HGI subgroup, suggesting that HbA1c may not be an appropriate indicator of BG control if it deviates too much from average BG, and this should be taken into account when making diabetes management decisions.

With the growing adoption of CGM as a diagnostic option for diabetes therapy, TIR has been recognized as an important metric to complement (or even replace) HbA1c, which can provide a complete picture of an individual's glucose control over time if combined with an indicator of exposure to hypo- or hyper-glycemia.[18,34,35] Furthermore, a recent reanalysis of the DCCT data has shown that TIR is strongly associated with the risk of microvascular complications from T1D,[36] with similar results found in type 2 diabetes as well,[37,38] and a case has been made for it to be accepted as an end point for clinical trials.[36] However, TIR is a reflection of BG measurements alone, thus revealing nonoptimal correlation with HbA1c.

In view of the above, it would be desirable to optimize a manner for correlating TIR and HbA1c by accounting for individualized gain in glycation relative to TIR.

Where applicable, citations herein refer to one or more of the documents listed in the section entitled "References."

The devices, systems, apparatuses, compositions, computer program products, non-transitory computer readable medium, models, algorithms, and methods of various embodiments disclosed herein may utilize aspects (e.g., devices, systems, apparatuses, compositions, computer program products, non-transitory computer readable medium, models, algorithms, and methods) disclosed in the following references, applications, publications and patents and which are hereby incorporated by reference herein in their entirety, and which are not admitted to be prior art with respect to embodiments herein by inclusion in this section:

1. U.S. Utility patent application Ser. No. 16/588,881, entitled "Tracking the Probability for Imminent Hypoglycemia in Diabetes from Self-Monitoring Blood Glucose (SMBG) Data", filed Sep. 30, 2019.
2. U.S. Utility patent application Ser. No. 13/394,091, entitled "Tracking the Probability for Imminent Hypoglycemia in Diabetes from Self-Monitoring Blood Glucose (SMBG) Data", filed Mar. 2, 2012; U.S. Pat. No. 10,431,342, issued Oct. 1, 2019.
3. International Patent Application Serial No. PCT/US2010/047711, entitled "Tracking the Probability for Imminent Hypoglycemia in Diabetes from Self-Monitoring Blood Glucose (SMBG) Data", filed Sep. 2, 2010; Publication No. WO 2011/028925, Mar. 10, 2011.
4. U.S. Utility patent application Ser. No. 16/583,456, entitled "SYSTEM, METHOD, AND COMPUTER READABLE MEDIUM FOR DYNAMIC INSULIN SENSITIVITY IN DIABETIC PUMP USERS", filed Sep. 26, 2019.
5. International Patent Application Serial No. PCT/US2016/050109, entitled "SYSTEM, METHOD, AND COMPUTER READABLE MEDIUM FOR DYNAMIC INSULIN SENSITIVITY IN DIABETIC PUMP USERS", filed Sep. 2, 2016; Publication No. WO 2017/040927, Mar. 9, 2017.
6. U.S. Utility patent application Ser. No. 15/255,828, entitled "SYSTEM, METHOD, AND COMPUTER READABLE MEDIUM FOR DYNAMIC INSULIN SENSITIVITY IN DIABETIC PUMP USERS", filed Sep. 2, 2016; U.S. Pat. No. 10,463,789, issued Nov. 5, 2019.
7. U.S. Utility patent application Ser. No. 16/546,335, entitled "System Coordinator and Modular Architecture for Open-Loop and Closed-Loop Control of Diabetes", filed Aug. 21, 2019.
8. U.S. Utility patent application Ser. No. 13/322,943, entitled "System Coordinator and Modular Architecture for Open-Loop and Closed-Loop Control of Diabetes", filed Nov. 29, 2011; U.S. Pat. No. 10,420,489, issued Sep. 24, 2019.
9. International Patent Application Serial No. PCT/US2010/036629, entitled "System Coordinator and Modular Architecture for Open-Loop and Closed-Loop Control of Diabetes", filed May 28, 2010; Publication No. WO 2010/138848, Dec. 2, 2010.
10. U.S. Utility patent application Ser. No. 16/451,766, entitled "TRACKING CHANGES IN AVERAGE GLYCEMIA IN DIABETICS", filed Jun. 25, 2019; Publication No. US-2019-0318801-A1, Oct. 17, 2019.
11. U.S. Utility patent application Ser. No. 14/769,638, entitled "METHOD AND SYSTEM FOR MODEL-BASED TRACKING OF CHANGES IN AVERAGE GLYCEMIA IN DIABETES", filed Aug. 21, 2015; U.S. Pat. No. 10,332,615, issued Jun. 25, 2019.
12. International Patent Application Serial No. PCT/US2014/017754, entitled "METHOD AND SYSTEM FOR MODEL-BASED TRACKING OF CHANGES IN AVERAGE GLYCEMIA IN DIABETES", filed Feb. 21, 2014; Publication No. WO 2014/130841, Aug. 28, 2014.
13. U.S. Utility patent application Ser. No. 16/126,879, entitled "Method, System and Computer Program Product for Evaluation of Insulin Sensitivity, Insulin/Carbohydrate Ratio, and Insulin Correction Factors in Diabetes from Self-Monitoring Data", filed Sep. 10, 2018; Publication No. US-2019-0019571-A1, Jan. 17, 2019.
14. U.S. Utility patent application Ser. No. 12/665,149, entitled "Method, System and Computer Program Product for Evaluation of Insulin Sensitivity, Insulin/Carbohydrate Ratio, and Insulin Correction Factors in Diabetes from Self-Monitoring Data", filed Dec. 17, 2009; Publication No. 2010/0198520, Aug. 5, 2010.
15. International Patent Application Serial No. PCT/US2008/069416, entitled "Method, System and Computer Program Product for Evaluation of Insulin Sensitivity, Insulin/Carbohydrate Ratio, and Insulin Correction Factors in Diabetes from Self-Monitoring Data", filed Jul. 8, 2008; Publication No. WO 2009/009528, Jan. 15, 2009.
16. U.S. Utility patent application Ser. No. 15/958,257, entitled "System, Method and Computer Readable Medium for Dynamical Tracking of the Risk for Hypoglycemia in Type 1 and Type 2 Diabetes", filed Apr. 20, 2018; Publication No. US-2018-0366223-A1, Dec. 20, 2018.
17. International Patent Application Serial No. PCT/US2016/058234, entitled "System, Method and Computer Readable Medium for Dynamical Tracking of the Risk for Hypoglycemia in Type 1 and Type 2 Diabetes", filed Oct. 21, 2016; Publication No. WO 2017/070553, Apr. 27, 2017.
18. U.S. Utility patent application Ser. No. 15/866,384, entitled "Method, System and Computer Program Product for Real-Time Detection of Sensitivity Decline in Analyte Sensors", filed Jan. 9, 2018; Publication No. US-2018-0323882-A1, Nov. 8, 2018.
19. U.S. Utility patent application Ser. No. 14/266,612, entitled "Method, System and Computer Program Product for Real-Time Detection of Sensitivity Decline in Analyte Sensors", filed Apr. 30, 2014; U.S. Pat. No. 9,882,660, issued Jan. 30, 2018.
20. U.S. Utility patent application Ser. No. 13/418,305, entitled "Method, System and Computer Program Product for Real-Time Detection of Sensitivity Decline in Analyte Sensors", filed Mar. 12, 2012; U.S. Pat. No. 8,718,958, issued May 6, 2014.
21. International Patent Application Serial No. PCT/US2007/082744, entitled "Method, System and Computer Program Product for Real-Time Detection of Sensitivity Decline in Analyte Sensors", filed Oct. 26, 2007; Publication No. WO/2008/052199, May 2, 2008.
22. U.S. Utility patent application Ser. No. 11/925,689, entitled "Method, System and Computer Program Product for Real-Time Detection of Sensitivity Decline in Analyte Sensors", filed Oct. 26, 2007; U.S. Pat. No. 8,135,548, issued Mar. 13, 2012.
23. U.S. Utility patent application Ser. No. 15/580,935, entitled "INSULIN MONITORING AND DELIVERY SYSTEM AND METHOD FOR CGM BASED FAULT DETECTION AND MITIGATION VIA METABOLIC STATE TRACKING", filed Dec. 8, 2017; Publication No. US-2019-0254595-A1, Aug. 22, 2019.
24. International Patent Application Serial No. PCT/US2016/036729, entitled "INSULIN MONITORING AND DELIVERY SYSTEM AND METHOD FOR CGM BASED FAULT DETECTION AND MITIGATION VIA METABOLIC STATE TRACKING", filed Jun. 9, 2016; Publication No. WO 2016/201120, Dec. 15, 2016.

25. U.S. Utility patent application Ser. No. 15/580,915, entitled "System and Method for Tracking Changes in Average Glycemia in Diabetics", filed Dec. 8, 2017; Publication No. US-2018-0313815-A1, Nov. 1, 2018.
26. International Patent Application Serial No. PCT/US2016/036481, entitled "System and Method for Tracking Changes in Average Glycemia in Diabetics", filed Jun. 8, 2016; Publication No. WO2016200970, Dec. 15, 2016.
27. U.S. Utility patent application Ser. No. 15/669,111, entitled "METHOD, SYSTEM AND COMPUTER PROGRAM PRODUCT FOR CGM-BASED PREVENTION OF HYPOGLYCEMIA VIA HYPOGLYCEMIA RISK ASSESSMENT AND SMOOTH REDUCTION INSULIN DELIVERY", filed Aug. 4, 2017; Publication No. US-2017-0337348-A1, Nov. 23, 2017.
28. U.S. Utility patent application Ser. No. 15/510,878, entitled "ACCURACY CONTINUOUS GLUCOSE MONITORING METHOD, SYSTEM, AND DEVICE", filed Mar. 13, 2017; Publication No. US-2017-0273607-A1, Sep. 28, 2017.
29. International Patent Application Serial No. PCT/US2015/045340, entitled "IMPROVED ACCURACY CONTINUOUS GLUCOSE MONITORING METHOD, SYSTEM, AND DEVICE", filed Aug. 14, 2015; Publication No. WO2016025874, Feb. 18, 2016.
30. U.S. Utility patent application Ser. No. 15/109,682, entitled "Central Data Exchange Node For System Monitoring and Control of Blood Glucose Levels in Diabetic Patients", filed Jul. 5, 2016; Publication No. US-2016-0331310-AI, Nov. 17, 2016.
31. International Patent Application Serial No. PCT/US2015/010167, entitled "Central Data Exchange Node For System Monitoring and Control of Blood Glucose Levels in Diabetic Patients", filed Jan. 5, 2015; Publication No. WO2015103543, Jul. 9, 2015.
32. U.S. Utility patent application Ser. No. 14/902,731, entitled "SIMULATION OF ENDOGENOUS AND EXOGENOUS GLUCOSE/INSULIN/GLUCAGON INTERPLAY IN TYPE 1 DIABETIC PATIENTS", filed Jan. 4, 2016; U.S. Pat. No. 10,169,544, issued Jan. 1, 2019.
33. International Patent Application Serial No. PCT/US2014/045393, entitled "SIMULATION OF ENDOGENOUS AND EXOGENOUS GLUCOSE/INSULIN/GLUCAGON INTERPLAY IN TYPE 1 DIABETIC PATIENTS", filed Jul. 3, 2014; Publication No. WO2015003124, Jan. 8, 2015.
34. U.S. Utility patent application Ser. No. 14/799,329, entitled "ACCURACY OF CONTINUOUS GLUCOSE SENSORS", filed Jul. 14, 2015; U.S. Pat. No. 10,194,850, issued Feb. 5, 2019.
35. U.S. Utility patent application Ser. No. 12/065,257, entitled "Accuracy of Continuous Glucose Sensors", filed Feb. 28, 2008; Publication No. 2008/0314395, Dec. 25, 2008.
36. International Patent Application Serial No. PCT/US2006/033724, entitled "Method for Improvising Accuracy of Continuous Glucose Sensors and a Continuous Glucose Sensor Using the Same", filed Aug. 29, 2006; Publication No. WO07027691, Mar. 8, 2007.
37. U.S. Utility patent application Ser. No. 14/419,375, entitled "COMPUTER SIMULATION FOR TESTING AND MONITORING OF TREATMENT STRATEGIES FOR STRESS HYPERGLYCEMIA", filed Feb. 3, 2015; U.S. Pat. No. 10,438,700, issued Oct. 8, 2019.
38. International Patent Application Serial No. PCT/US2013/053664, entitled "COMPUTER SIMULATION FOR TESTING AND MONITORING OF TREATMENT STRATEGIES FOR STRESS HYPERGLYCEMIA", filed Aug. 5, 2013; Publication No. WO 2014/022864, Feb. 6, 2014.
39. U.S. Utility patent application Ser. No. 14/241,383, entitled "Method, System and Computer Readable Medium for Adaptive Advisory Control of Diabetes", filed Feb. 26, 2014; Publication No. 2015-0190098, Jul. 9, 2015.
40. International Patent Application Serial No. PCT/US2012/052422, entitled "Method, System and Computer Readable Medium for Adaptive Advisory Control of Diabetes", filed Aug. 26, 2012; Publication No. WO 2013/032965, Mar. 7, 2013.
41. U.S. Utility patent application Ser. No. 14/128,922, entitled "Unified Platform For Monitoring and Control of Blood Glucose Levels in Diabetic Patients", filed Dec. 23, 2013; Publication No. 2015/0018633, Jan. 15, 2015.
42. International Patent Application Serial No. PCT/US2012/043910, entitled "Unified Platform For Monitoring and Control of Blood Glucose Levels in Diabetic Patients", filed Jun. 23, 2012; Publication No. WO 2012/178134, Dec. 27, 2012.
43. U.S. Utility patent application Ser. No. 14/128,811, entitled "Methods and Apparatus for Modular Power Management and Protection of Critical Services in Ambulatory Medical Devices", filed Dec. 23, 2013; U.S. Pat. No. 9,430,022, issued Aug. 30, 2016.
44. International Patent Application Serial No. PCT/US2012/043883, entitled "Methods and Apparatus for Modular Power Management and Protection of Critical Services in Ambulatory Medical Devices", filed Jun. 22, 2012; Publication No. WO 2012/178113, Dec. 27, 2012.
45. U.S. Utility patent application Ser. No. 29/467,039, entitled "Alarm Clock Display of Personal Blood Glucose Level", filed Sep. 13, 2013.
46. U.S. Utility patent application Ser. No. 14/015,831, entitled "CGM-Based Prevention of Hypoglycemia Via Hypoglycemia Risk Assessment and Smooth Reduction of Insulin Delivery", filed Aug. 30, 2013; U.S. Pat. No. 9,750,438, issued Sep. 5, 2017.
47. U.S. Utility patent application Ser. No. 13/203,469, entitled "CGM-Based Prevention of Hypoglycemia via Hypoglycemia Risk Assessment and Smooth Reduction Insulin Delivery", filed Aug. 25, 2011; U.S. Pat. No. 8,562,587, issued Oct. 22, 2013.
48. International Patent Application Serial No. PCT/US2010/025405, entitled "CGM-BASED PREVENTION OF HYPOGLYCEMIA VIA HYPOGLYCEMIA RISK ASSESMENT AND SMOOTH REDUCTION INSULIN DELIVERY", filed Feb. 25, 2010; Publication No. WO 2010/099313 A1, Sep. 2, 2010.
49. International Patent Application Serial No. PCT/US2013/042745, entitled "INSULIN-PRAMLINTIDE COMPOSITIONS AND METHODS FOR MAKING AND USING THEM", filed May 24, 2013; Publication No. WO 2013/177565, Nov. 28, 2013.
50. U.S. Utility patent application Ser. No. 13/637,359, entitled "METHOD, SYSTEM, AND COMPUTER PROGRAM PRODUCT FOR IMPROVING THE ACCURACY OF GLUCOSE SENSORS USING INSULIN DELIVERY OBSERVATION IN DIABETES", filed Sep. 25, 2012; U.S. Pat. No. 9,398,869, issued Jul. 26, 2016.
51. International Patent Application Serial No. PCT/US2011/029793, entitled "METHOD, SYSTEM, AND COMPUTER PROGRAM PRODUCT FOR IMPROVING THE ACCURACY OF GLUCOSE SENSORS USING INSULIN DELIVERY OBSERVATION IN DIABETES", filed Mar. 24, 2011; Publication No. WO 2011/119832, Sep. 29, 2011.

52. U.S. Utility patent application Ser. No. 13/634,040, entitled "Method and System for the Safety, Analysis, and Supervision of Insulin Pump Action and Other Modes of Insulin Delivery in Diabetes", filed Sep. 11, 2012; Publication No. 2013/0116649, May 9, 2013.

53. International Patent Application Serial No. PCT/US2011/028163, entitled "Method and System for the Safety, Analysis, and Supervision of Insulin Pump Action and Other Modes of Insulin Delivery in Diabetes", filed Mar. 11, 2011; Publication No. WO 2011/112974, Sep. 15, 2011.

54. U.S. Utility patent application Ser. No. 13/393,647, entitled "System, Method and Computer Program Product for Adjustment of Insulin Delivery (AID) in Diabetes Using Nominal Open-Loop Profiles", filed Mar. 1, 2012; Publication No. 2012/0245556, Sep. 27, 2012.

55. International Patent Application Serial No. PCT/US2010/047386, entitled "System, Method and Computer Program Product for Adjustment of Insulin Delivery (AID) in Diabetes Using Nominal Open-Loop Profiles", filed Aug. 31, 2010; Publication No. WO 2011/028731, Mar. 10, 2011.

56. U.S. Utility patent application Ser. No. 13/380,839, entitled "System, Method, and Computer Simulation Environment for In Silico Trials in Pre-Diabetes and Type 2 Diabetes", filed Dec. 25, 2011; Publication No. 2012/0130698, May 24, 2012.

57. International Patent Application Serial No. PCT/US2010/040097, entitled "System, Method, and Computer Simulation Environment for In Silico Trials in Prediabetes and Type 2 Diabetes", filed Jun. 25, 2010; Publication No. WO 2010/151834, Dec. 29, 2010.

58. U.S. Utility patent application Ser. No. 13/131,467, entitled "Method, System, and Computer Program Product for Tracking of Blood Glucose Variability in Diabetes", filed May 26, 2011; U.S. Pat. No. 9,317,657, issued Apr. 19, 2016.

59. International Patent Application Serial No. PCT/US2009/065725, entitled "Method, System, and Computer Program Product for Tracking of Blood Glucose Variability in Diabetes", filed Nov. 24, 2009; Publication No. WO 2010/062898, Jun. 3, 2010.

60. U.S. Utility patent application Ser. No. 12/975,580, entitled "Method, System, and Computer Program Product for the Evaluation of Glycemic Control in Diabetes from Self-Monitoring Data", filed Dec. 22, 2010; Publication No. 2012/0004512, Jan. 5, 2012.

61. U.S. Utility patent application Ser. No. 11/305,946, entitled "Method, System, and Computer Program Product for the Evaluation of Glycemic Control in Diabetes from Self-Monitoring Data", filed Dec. 19, 2005; U.S. Pat. No. 7,874,985, issued Jan. 25, 2011.

62. U.S. Utility patent application Ser. No. 10/240,228, entitled "Method, System, and Computer Program Product for the Evaluation of Glycemic Control in Diabetes from Self-Monitoring Data", filed Sep. 26, 2002; U.S. Pat. No. 7,025,425, issued Apr. 11, 2006.

63. International Patent Application Serial No. PCT/US2001/009884, entitled "Method, System, and Computer Program Product for the Evaluation of Glycemic Control in Diabetes", filed Mar. 29, 2001; Publication No. WO 01/72208, Oct. 4, 2001.

64. U.S. Utility patent application Ser. No. 12/674,348, entitled "Method, Computer Program Product and System for Individual Assessment of Alcohol Sensitivity", filed Feb. 19, 2010; Publication No. 2011/0264374, Oct. 27, 2011.

65. International Patent Application Serial No. PCT/US2008/073738, entitled "Method, Computer Program Product and System for Individual Assessment of Alcohol Sensitivity", filed Aug. 20, 2008; Publication No. WO 2009/026381, Feb. 26, 2009.

66. U.S. Utility patent application Ser. No. 12/664,444, entitled "Method, System and Computer Simulation Environment for Testing of Monitoring and Control Strategies in Diabetes", filed Dec. 14, 2009; Publication No. 2010/0179768, Jul. 15, 2010.

67. International Patent Application Serial No. PCT/US2008/067725, entitled "Method, System and Computer Simulation Environment for Testing of Monitoring and Control Strategies in Diabetes", filed Jun. 20, 2008; Publication No. WO 2008/157781, Dec. 24, 2008.

68. U.S. Utility patent application Ser. No. 12/516,044, entitled "Method, System, and Computer Program Product for the Detection of Physical Activity by Changes in Heart Rate, Assessment of Fast Changing Metabolic States, and Applications of Closed and Open Control Loop in Diabetes", filed May 22, 2009; U.S. Pat. No. 8,585,593, issued Nov. 19, 2013.

69. International Patent Application Serial No. PCT/US2007/085588, entitled "Method, System, and Computer Program Product for the Detection of Physical Activity by Changes in Heart Rate, Assessment of Fast Changing Metabolic States, and Applications of Closed and Open Control Loop in Diabetes", filed Nov. 27, 2007; Publication No. WO2008/067284, Jun. 5, 2008.

70. U.S. Utility patent application Ser. No. 12/159,891, entitled "Method, System and Computer Program Product for Evaluation of Blood Glucose Variability in Diabetes from Self-Monitoring Data", filed Jul. 2, 2008; Publication No. 2009/0171589, Jul. 2, 2009.

71. International Patent Application Serial No. PCT/US2007/000370, entitled "Method, System and Computer Program Product for Evaluation of Blood Glucose Variability in Diabetes from Self-Monitoring Data", filed Jan. 5, 2007; Publication No. WO07081853, Jul. 19, 2007.

72. U.S. Utility patent application Ser. No. 12/139,976, entitled "Method, Apparatus and Computer Program Product for Assessment of Attentional Impairments", filed Jun. 16, 2008; U.S. Pat. No. 8,340,752, issued Dec. 25, 2012.

73. U.S. Utility patent application Ser. No. 10/476,826, entitled "Method, Apparatus, and Computer Program Product for Assessment of Attentional Impairments", filed Nov. 3, 2003; U.S. Pat. No. 7,403,814, issued Jul. 22, 2008.

74. International Patent Application Serial No. US02/14188, entitled "METHOD, APPARATUS, AND COMPUTER PROGRAM PRODUCT FOR ASSESSMENT OF ATTENTIONAL IMPAIRMENTS", filed May 6, 2002; Publication No. WO02091119, Nov. 14, 2002.

75. U.S. Utility patent application Ser. No. 11/943,226, entitled "Systems, Methods and Computer Program Codes for Recognition of Patterns of Hyperglycemia and Hypoglycemia, Increased Glucose Variability, and Ineffective Self-Monitoring in Diabetes", filed Nov. 20, 2007; Publication No. 2008/0154513, Jun. 26, 2008.

76. U.S. Utility patent application Ser. No. 11/578,831, entitled "Method, System and Computer Program Product for Evaluating the Accuracy of Blood Glucose Monitoring Sensors/Devices", filed Oct. 18, 2006; U.S. Pat. No. 7,815,569, issued Oct. 19, 2010.
77. International Patent Application Serial No. US2005/013792, entitled "Method, System and Computer Program Product for Evaluating the Accuracy of Blood Glucose Monitoring Sensors/Devices", filed Apr. 21, 2005; Publication No. WO05106017, Nov. 10, 2005.
78. U.S. Utility patent application Ser. No. 10/592,883, entitled "Method, Apparatus, and Computer Program Product for Stochastic Psycho-physiological Assessment of Attentional Impairments", filed Sep. 15, 2006; U.S. Pat. No. 7,761,144, issued Jul. 20, 2010.
79. International Patent Application Serial No. US2005/008908, entitled "Method, Apparatus, and Computer Program Product for Stochastic Psycho-physiological Assessment of Attentional Impairments", filed Mar. 17, 2005; Publication No. 2005089431, Sep. 29, 2005.
80. U.S. Utility patent application Ser. No. 10/524,094, entitled "Method, System, And Computer Program Product For The Processing Of Self-Monitoring Blood Glucose (SMBG) Data To Enhance Diabetic Self-Management", filed Feb. 9, 2005; U.S. Pat. No. 8,538,703, issued Sep. 17, 2013.
81. International Patent Application Serial No. PCT/US2003/025053, entitled "Managing and Processing Self-Monitoring Blood Glucose", filed Aug. 8, 2003; Publication No. WO 2004/015539, Feb. 19, 2004.
82. International Patent Application Serial No. PCT/US2002/005676, entitled "METHOD AND APPARATUS FOR THE EARLY DIAGNOSIS OF SUBACUTE, POTENTIALLY CATASTROPHIC ILLNESS", filed Feb. 27, 2002; Publication No. WO02/67776, Sep. 6, 2002.
83. U.S. Utility patent application Ser. No. 09/793,653, entitled "METHOD AND APPARATUS FOR THE EARLY DIAGNOSIS OF SUBACUTE, POTENTIALLY CATASTROPHIC ILLNESS", filed Feb. 27, 2001; Publication No. 2002/0052557, May 2, 2002.
84. U.S. Utility patent application Ser. No. 10/069,674, entitled "Method and Apparatus for Predicting the Risk of Hypoglycemia", filed Feb. 22, 2002; U.S. Pat. No. 6,923,763, issued Aug. 2, 2005.
85. International Patent Application Serial No. US00/22886, entitled "METHOD AND APPARATUS FOR PREDICTING THE RISK OF HYPOGLYCEMIA", filed Aug. 21, 2000; Publication No. WO01/13786, Mar. 1, 2001.

SUMMARY

It is to be understood that both the following summary and the detailed description are exemplary and explanatory and are intended to provide further explanation of the present embodiments as claimed. Neither the summary nor the description that follows is intended to define or limit the scope of the present embodiments to the particular features mentioned in the summary or in the description. Rather, the scope of the present embodiments is defined by the appended claims.

In this regard, embodiments herein provide correlation between blood glucose (BG) fluctuation evinced by CGM-TIR and HbA1c. To do so, such embodiments furnish a dynamical model of hemoglobin glycation and clearance which is calibrated to a sole measure of laboratory HbA1c to capture an individual glycation rate. Accordingly, the model may, when implemented with available CGM technologies, offer a real-time (e.g. daily) projection of laboratory HbA1c, which has been shown to be accurate up to 9 months following the initial calibration (Fabris C, 2020).

An embodiment may include a processor-implemented method for providing a real-time estimation of laboratory glycosylated hemoglobin (HbA1c) of a patient at one or more intervals (e.g. daily), as a value of estimated A1c (eA1c) based on continuous glucose monitoring (CGM)-derived time in target range (TIR) (CGM-TIR) for the patient, in which the method may include receiving and storing in a memory one or more values of laboratory HbA1c, and calculating said value of eA1c for a respective one of said one or more intervals in accordance with one or more processors configured to (a) receive and store in said memory daily CGM-TIR data of said patient, (b) transform said received daily CGM-TIR data into units corresponding to said values of HbA1c, (c) determine a glycation rate of said patient based on a respective one of said values of HbA1c of said patient, and (d) adjust said transformed CGM-TIR data based on said determined glycation rate.

The received CGM-TIR data may be fed to a predetermined glycation equation to obtain said transformation of said received CGM-TIR data.

The predetermined glycation equation may be given by:

$$\frac{\partial eA1c}{\partial t} = \frac{-1}{\tau}\left(eA1c - \gamma \cdot f_{CGM-TIR}\right),$$

where eA1c is estimated A1c, $\partial$eA1c/$\partial$t is a derivate of the eA1c, $\tau$ is a clearance rate of the eA1c, $f_{CGM-TIR}$ is a linear function of the received daily CGM-TIR data for a target range thereof of 70-180 mg/dL, in which $f_{CGM-TIR}=m \cdot CGM\text{-}TIR+q$, and $\tau$, m, and q are population based parameter values which are determined for a given value of HbA1c measured outside of said predetermined intervals and generic to the patient, and $\gamma$ is a parameter value specific to the patient for yielding said glycation rate to modulate glycation gain to allow a lower or a higher value of eA1c for a same value of $f_{CGM-TIR}$.

The parameter value $\gamma$ may be determined for an individual one of the one or more predetermined intervals preceding another of the one or more predetermined intervals.

The parameter value $\gamma$ may be determined based on the respective one of the values of laboratory HbA1c, wherein the respective value corresponds to the individual one of the one or more predetermined intervals preceding another of the one or more predetermined intervals.

The method may further include comparing the value of eA1c to one of the values of HbA1c, for a respectively corresponding one of the one or more predetermined intervals, to determine a relative difference therebetween.

Respective embodiments may further include a relative system and a computer-readable medium commensurate with the embodied method above.

In certain embodiments, the disclosed embodiments may include one or more of the features described herein.

BRIEF DESCRIPTION OF THE DRAWINGS

The accompanying drawings, which are incorporated herein and form a part of the specification, illustrate exemplary embodiments and, together with the description, further serve to enable a person skilled in the pertinent art to make and use these embodiments and others that will be apparent to those skilled in the art. Embodiments herein will be more particularly described in conjunction with the following drawings wherein.

DETAILED DESCRIPTION

Figure 1:
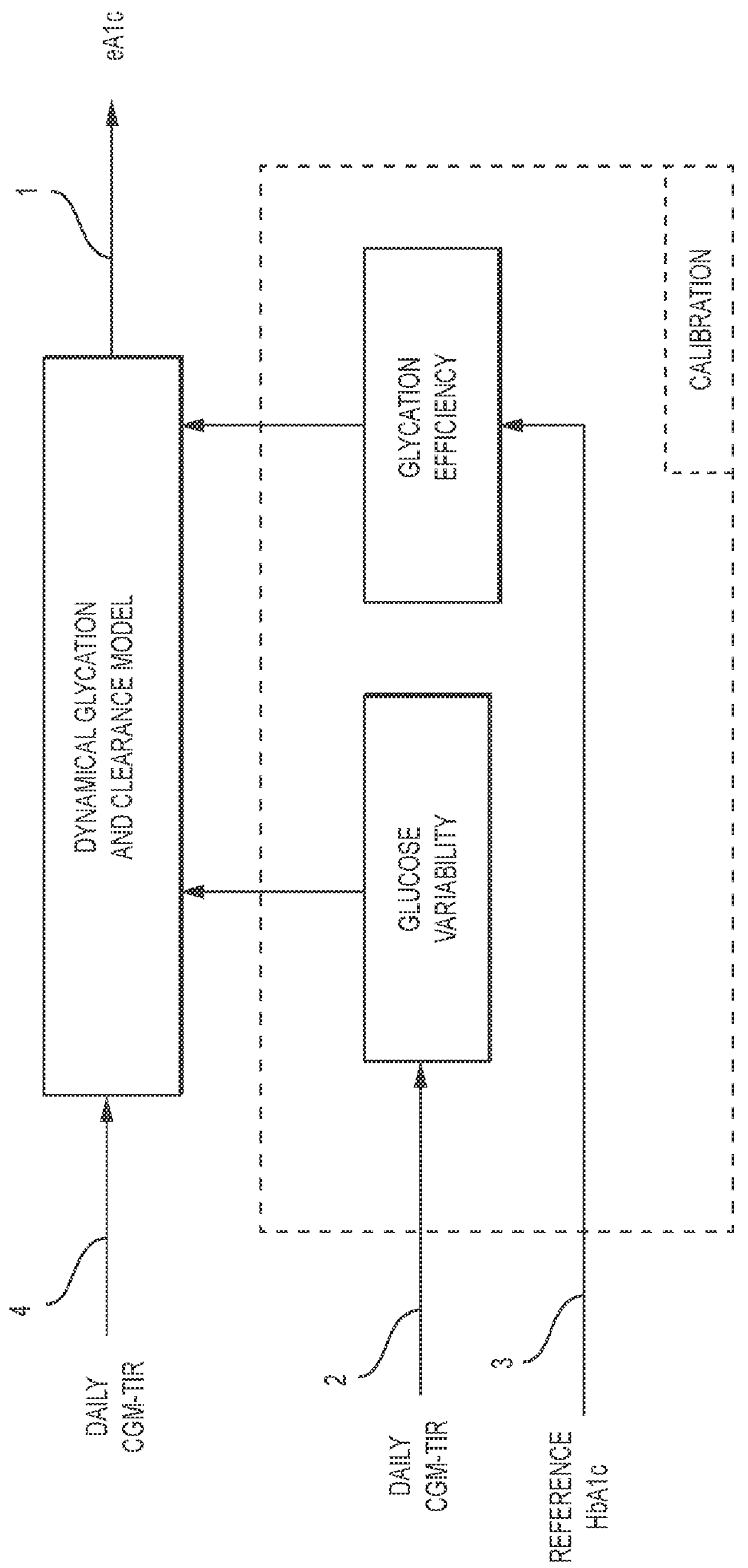
FIG. 1 illustrates a schematic diagram of a system architecture of production of estimated A1c (eA1c), according to embodiments herein.

The present disclosure will now be described in terms of various exemplary embodiments. This specification discloses one or more embodiments that incorporate features of the present embodiments. The embodiment(s) described, and references in the specification to "one embodiment", "an embodiment", "an example embodiment", etc., indicate that the embodiment(s) described may include a particular feature, structure, or characteristic. Such phrases are not necessarily referring to the same embodiment. The skilled artisan will appreciate that a particular feature, structure, or characteristic described in connection with one embodiment is not necessarily limited to that embodiment but typically has relevance and applicability to one or more other embodiments.

In the several figures, like reference numerals may be used for like elements having like functions even in different drawings. The embodiments described, and their detailed construction and elements, are merely provided to assist in a comprehensive understanding of the present embodiments. Thus, it is apparent that the present embodiments can be carried out in a variety of ways, and does not require any of the specific features described herein. Also, well-known functions or constructions are not described in detail since they would obscure the present embodiments with unnecessary detail.

The description is not to be taken in a limiting sense, but is made merely for the purpose of illustrating the general principles of the present embodiments, since the scope of the present embodiments are best defined by the appended claims.

It should also be noted that in some alternative implementations, the blocks in a flowchart, the communications in a sequence-diagram, the states in a state-diagram, etc., may occur out of the orders illustrated in the figures. That is, the illustrated orders of the blocks/communications/states are not intended to be limiting. Rather, the illustrated blocks/communications/states may be reordered into any suitable order, and some of the blocks/communications/states could occur simultaneously.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one" of "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedure, Section 2111.03.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. The word "exemplary" is used herein to mean "serving as an example, instance, or illustration." Any embodiment described herein as "exemplary" is not necessarily to be construed as preferred or advantageous over other embodiments. Additionally, all embodiments described herein should be considered exemplary unless otherwise stated.

It should be appreciated that any of the components or modules referred to with regards to any of the embodiments discussed herein, may be integrally or separately formed with one another. Further, redundant functions or structures of the components or modules may be implemented. Moreover, the various components may be communicated locally and/or remotely with any user/clinician/patient or machine/system/computer/processor. Moreover, the various components may be in communication via wireless and/or hardwire or other desirable and available communication means, systems and hardware. Moreover, various components and modules may be substituted with other modules or components that provide similar functions.

It should be appreciated that the device and related components discussed herein may take on all shapes along the entire continual geometric spectrum of manipulation of x, y and z planes to provide and meet the anatomical, environmental, and structural demands and operational requirements. Moreover, locations and alignments of the various components may vary as desired or required.

It should be appreciated that various sizes, dimensions, contours, rigidity, shapes, flexibility and materials of any of the components or portions of components in the various embodiments discussed throughout may be varied and utilized as desired or required.

It should be appreciated that while some dimensions are provided on the aforementioned figures, the device may constitute various sizes, dimensions, contours, rigidity, shapes, flexibility and materials as it pertains to the components or portions of components of the device, and therefore may be varied and utilized as desired or required.

Although example embodiments of the present disclosure are explained in some instances in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

Ranges may be expressed herein as from "about" or "approximately" one particular value and/or to "about" or "approximately" another particular value. When such a range is expressed, other exemplary embodiments include from the one particular value and/or to the other particular value.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

It should be appreciated that as discussed herein, a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g., a rat, dog, pig, or monkey), etc. It should be appreciated that the subject may be any applicable human patient, for example.

Some references, which may include various patents, patent applications, and publications, are cited in a reference list and discussed in the disclosure provided herein. The citation and/or discussion of such references is provided merely to clarify the description of the present disclosure and is not an admission that any such reference is "prior art" to any aspects of the present disclosure described herein. In terms of notation, "[n]" corresponds to the $n^{th}$ reference in the list. All references cited and discussed in this specification are incorporated herein by reference in their entireties and to the same extent as if each reference was individually incorporated by reference.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 10% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, 4.24, and 5). Similarly, numerical ranges recited herein by endpoints include subranges subsumed within that range (e.g. 1 to 5 includes 1-1.5, 1.5-2, 2-2.75, 2.75-3, 3-3.90, 3.90-4, 4-4.24, 4.24-5, 2-5, 3-5, 1-4, and 2-4). It is also to be understood that all numbers and fractions thereof are presumed to be modified by the term "about."

Referring to FIG. 1, there is shown a high-level schematic diagram of the flow of data informing the estimation of laboratory HbA1c and provided as estimated A1c (eA1c) 1 according to the eA1c dynamical model (eA1c DM) embodiments herein. At a high level, and as shown, the eA1c DM may be trained and calibrated, respectively, in accordance with CGM-derived time in target range (TIR), i.e., CGM-TIR data 2 (glucose variability) and a single, reference laboratory HbA1c 3 (glycation efficiency) to achieve the eA1c 1 as an expectation, i.e., projection, of laboratory HbA1c at a predetermined time post-calibration. In its simplest form, the eA1c DM may be implemented by one or more processors, as discussed later, according to mathematical modeling that is interpretative of CGM-TIR 4.

Figure 2:
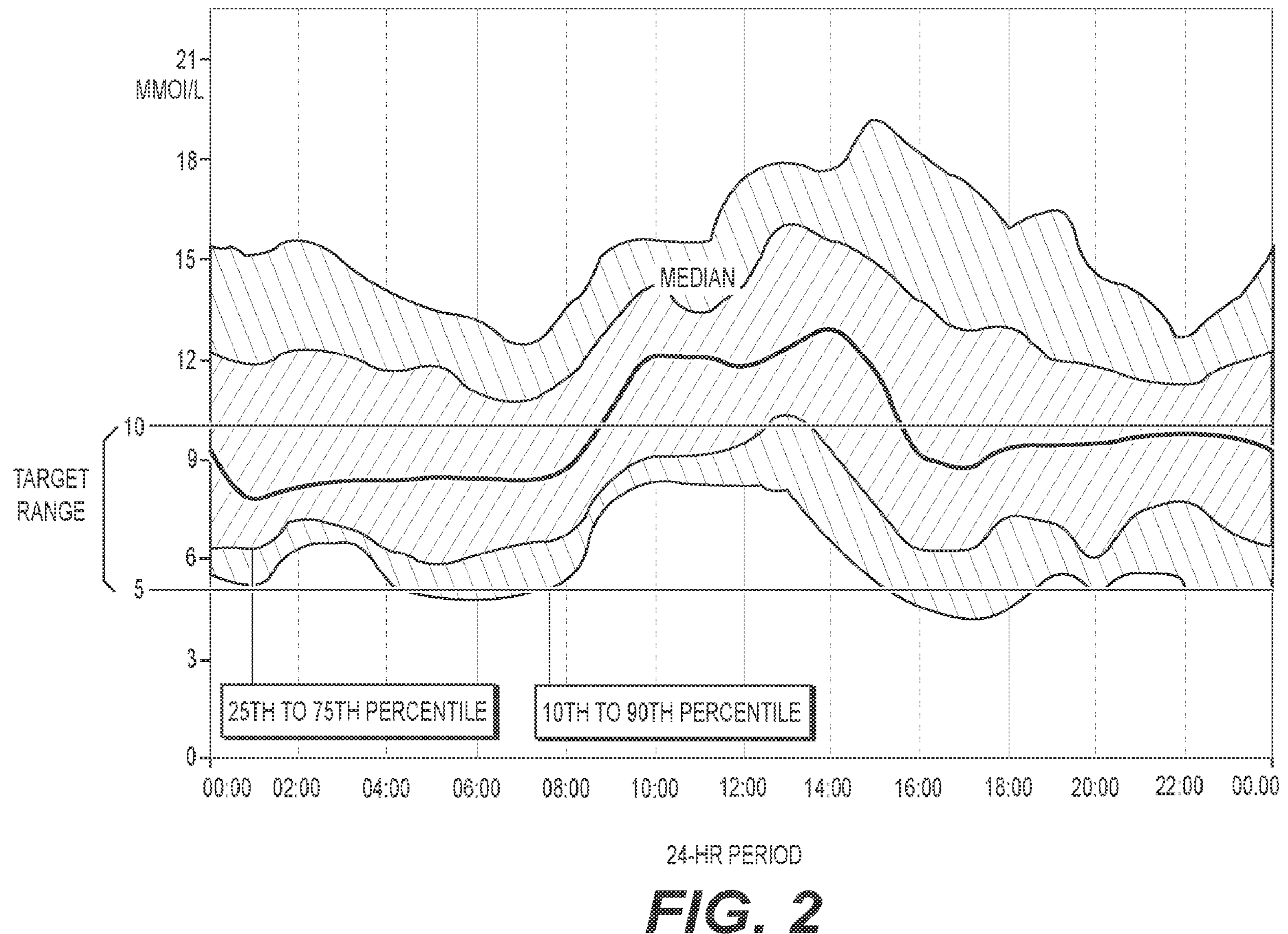
FIG. 2 illustrates an exemplary 24-hour CGM BG profile, relative to median and various percentile ranges therefor, according to embodiments herein.
Figure 3:
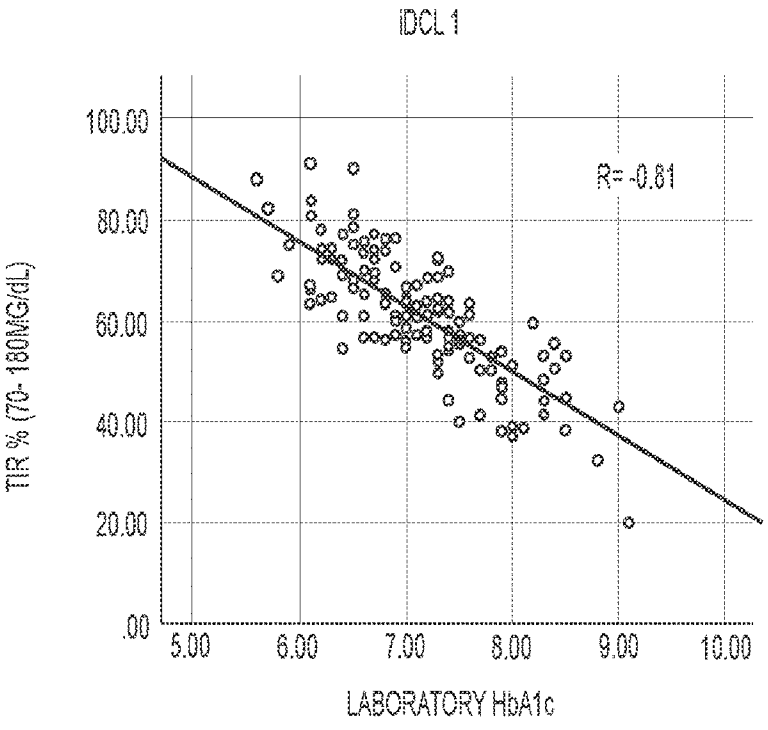
FIG. 3 illustrates, in accordance with International Diabetes Closed-Loop Trial (iDCL) Protocol 1 (iDCL 1), TIR (70-180 mg/dL) versus HbA1c.
Figure 4:
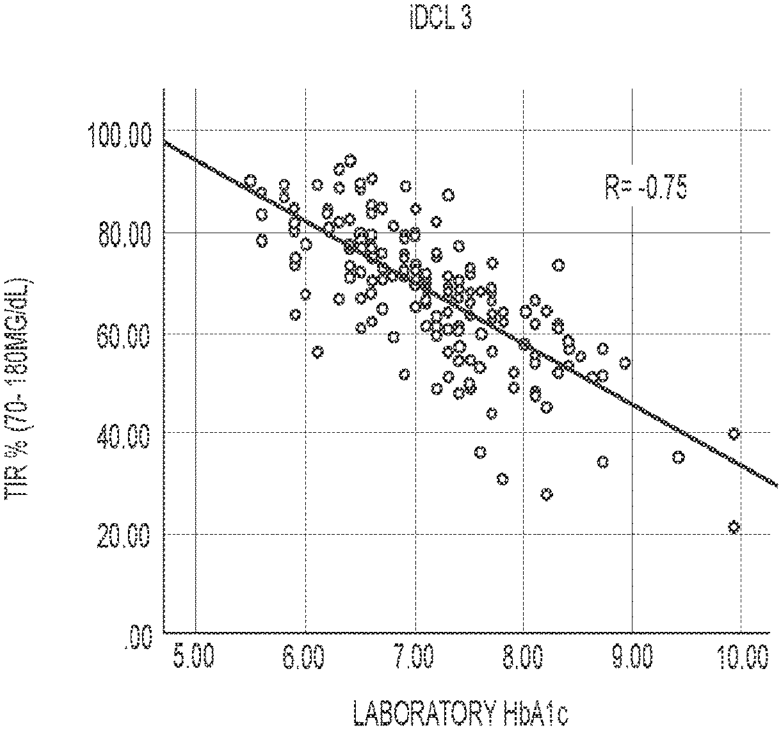
FIG. 4 illustrates, in accordance with iDCL Protocol 3 (iDCL 3), TIR (70-180 mg/dL) versus HbA1c.
Figure 5:
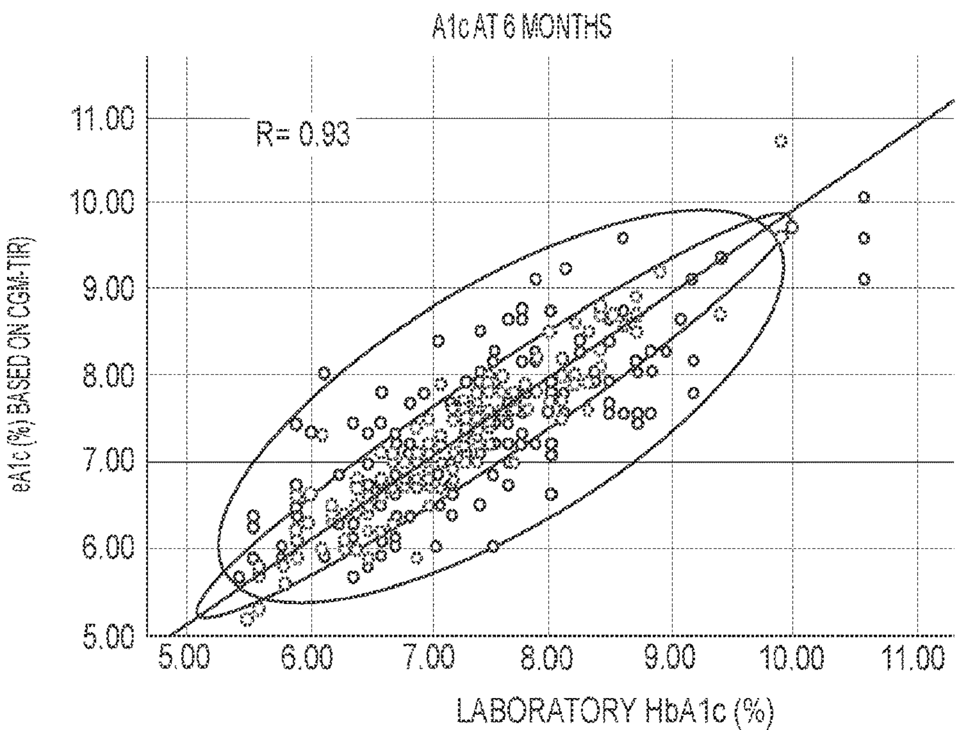
FIG. 5 illustrates, for iDCL 3 over a nine (9) month study period, 6-month correlation between laboratory HbA1c and estimated A1c (eA1c) derived from CGM-TIR, according to embodiments herein.
Figure 10:
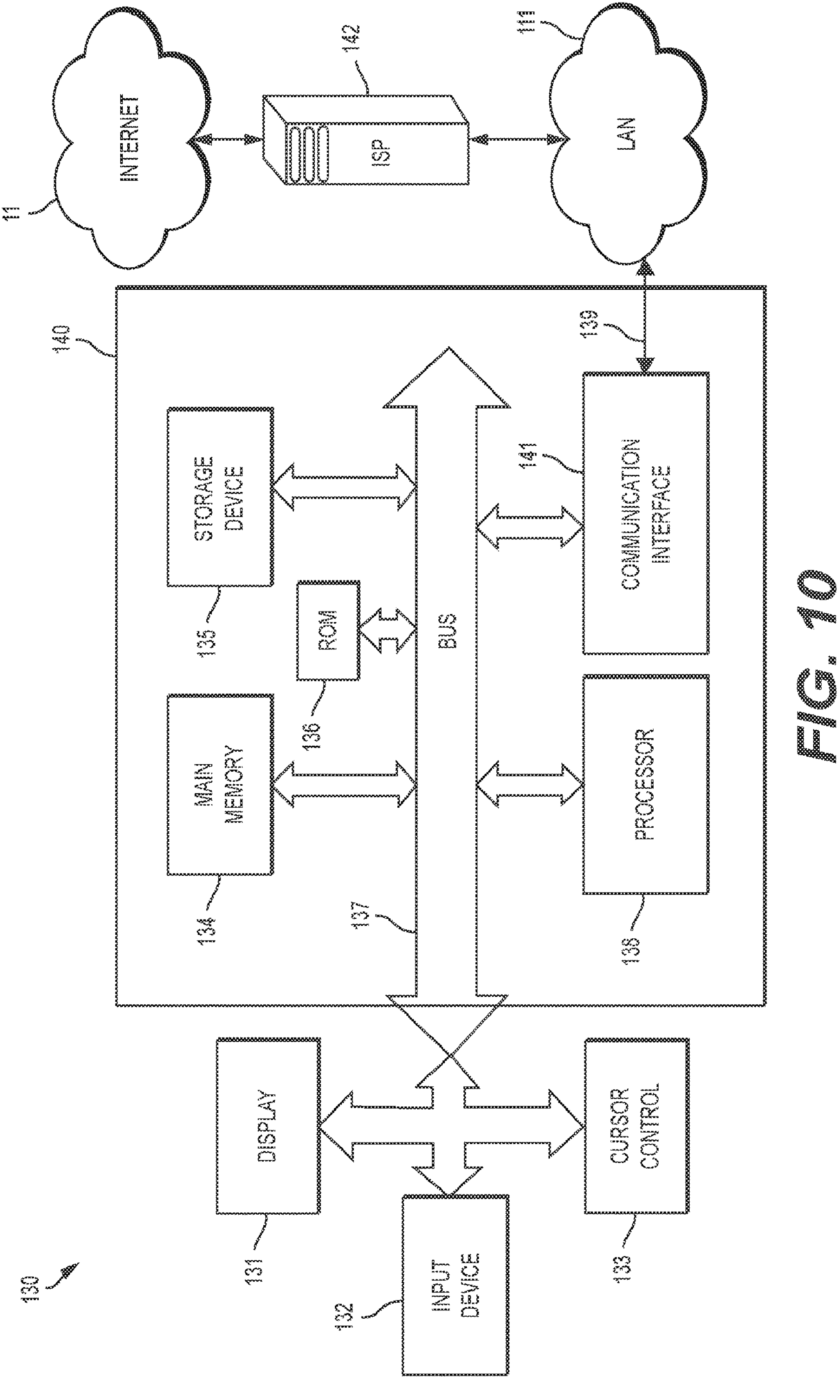
FIG. 10 illustrates a block diagram which may implement and/or be used in the implementation of the eA1c DM in association with a connection to the Internet.

Referring to FIG. 2, there is illustrated 24-hour CGM BG profile which may be derived from CGM profiles collected and processed daily by for example, CGM 10, according to FIG. 10. That is, the profile may be a representative average profile for a predetermined study period. Relative to individual physiology and eating habits, median and percentile characterizations in mmol/L are depicted based on the daily timeframe and with respect to target range. Such CGM profiles serve to inform CGM-TIR, with respect to determination of eA1c, as described herein. As will be appreciated by inspection of FIGS. 3 and 4 describing a level of Pearson's correlation (R) for TIR versus laboratory HbA1c, discordance therebetween is evident over time relative to iDCL 1[40] and iDCL 3[41]. As will also be appreciated and although A1c measurement and TIR may, according to embodiments herein, be demonstrated to indicate a same underlying process of glycemic fluctuation, reconciliation therebetween may contribute to diminishment of discordance. Exemplary reconciliation is exhibited in U.S. Pat. No. 10,332,615 to Kovatchev et al., the entirety of which is hereby incorporated by reference herein.

Embodiments as now described further achieve such reconciliation through implementation of the eA1c DM representing a dynamical model of hemoglobin glycation that is individualized according to a single laboratory HbA1c value for a patient in order to garner eA1c for that patient. In this regard, eA1c is presented so as to bridge the gap between CGM-TIR and laboratory HbA1c, while demonstrating that the two metrices are merely different representations of a same underlying process of glycemic fluctuation.

Accordingly, we, the present inventors' group at the University of Virginia, described hemoglobin glycation and clearance in terms of the eA1c DM represented by the first-order differential equation below, in which:

$$\frac{\partial eA1c}{\partial t} = \frac{-1}{\tau}\left(eA1c - \gamma \cdot f_{CGM-TIR}\right),$$

where eA1c represents estimated A1c, ∂eA1c/∂t represents its derivate, τ represents its clearance rate, and $f_{TIR}$ represents a linear function of CGM-TIR computed for each study day from CGM-TIR data having a target range of 70-180 mg/dL[39], which is modulated by the parameter γ. The driving function, $f_{TIR}$, may be defined in accordance with $f_{TIR}$=m·CGM-TIR+q. To adjust the eA1c DM to differences in red blood cell lifespan, γ is included as a patient-specific parameter value to modulate the model gain so as to allow for lower/higher eA1c values for the same value of the driving function $f_{TIR}$.

Thus, as will be appreciated, eA1c depends upon the above-noted parameters τ, m, q, and γ, whereas parameters τ, m, and q are population based so as to be the same for all individuals. Accordingly, the model parameters τ, m, and q may be estimated directly from available data, and fixed to population values, while parameter γ may be individualized according to a single laboratory HbA1c value.

In these regards, the eA1c DM underwent model training according to iDCL 1 and iDCL 3 and model testing or assessment according to iDCL 3, per the discussion below.

Model Training

Data collected as part of the iDCL 1[40] were used as training data to develop the model and estimate the three populations parameters τ, m, and q. The data set included CGM traces collected for 13 consecutive weeks in 125 adults with T1D, and laboratory HbA1c measured at a central laboratory at week 13. DEXCOM G4 or G5 CGM systems were used in the study, calibrated using fingerstick BG measurements per manufacturer's guidelines. The BG meter used for calibration of CGM systems was a CONTOUR NEXT ONE Blood Glucose Monitoring System. The eA1c DM was used to compute eA1c daily from CGM-TIR. The population parameters t, m, and q were estimated by running the model for the 3 months of CGM data to fit the laboratory HbA1c collected at week 13. The parameter values were then fixed. As such, the eA1c DM may achieve transformation of CGM-TIR into laboratory HbA1c units.

Data from the iDCL 3[41] were used as training data to with respect to calibration of the patient-specific parameter γ. The data set included CGM traces collected for 9 months in 168 adults with T1D, and laboratory HbA1c measured at a central laboratory at 3, 6, and 9 months. In this study, participants wore a DEXCOM G6 CGM system, which is a factory-calibrated device and, therefore, does not require fingerstick calibration. The first laboratory HbA1c collected at month 3 of the study was used to individualize the model by calibrating the patient-specific parameter γ to capture an individual glycation rate for a given patient, wherein such parameter γ was thereafter fixed to assess eA1c versus laboratory HbA1c, as discussed below.

Model Testing

Based on the iDCL 3 data accumulated during the 9 month period, accuracy of the eA1c DM was assessed subsequent to training of the model and resultant determination of parameters τ, m, q, and γ. In other words, laboratory HbA1c values post determination of the patient-specific parameter γ at month 3 of the study were compared to assess accuracy of the eA1c DM as trained. More specifically, eA1c values calculated by the eA1c DM at months 6 and 9 of the study were compared to laboratory HbA1c values measured at the same time periods. Further, to evaluate the influence of the duration of the pre-calibration CGM data collection on the accuracy of eA1c, run-in scenarios ranging from 1 to 12 weeks were assessed.

Results

Estimates of the model parameters τ, m, q, and γ are reported in Table 1 below, and reflect values implemented in the running of the eA1c DM at months 6 and 9 of the study.

TABLE 1

| POPULATION AND INDIVIDUAL PARAMETERS OF THE MODEL FOR THE DYNAMICAL ESTIMATION OF A1c | |
|---|---|
| Population parameters (estimated from the training data set) | |
| τ | 34.78 ± 7.26 |
| m | 10.19 ± 0.24 |
| q | −0.05 ± 0.004 |
| Individual parameter (estimated for each subject in the testing data set) | |
| γ | 1.04 ± 0.08 |

Population parameters are reported as estimate ± standard error of the estimate.
The individual parameter is reported as mean ± standard deviation across subjects.

Figure 6:
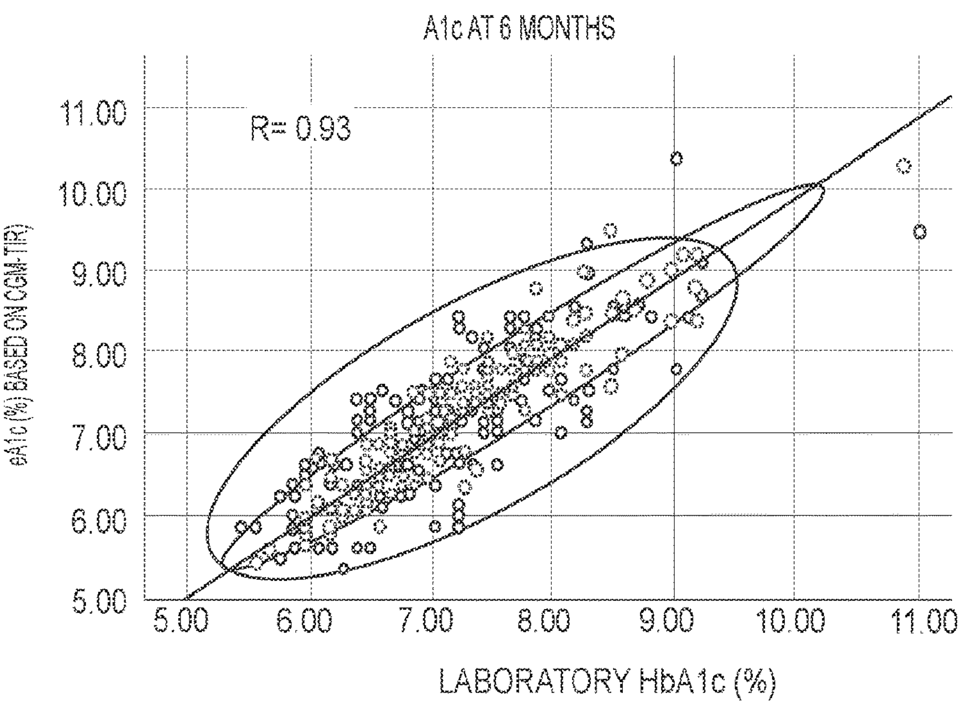
FIG. 6 illustrates, for iDCL 3 over a nine (9) month study period, 9-month correlation between laboratory HbA1c and estimated A1c (eA1c) derived from CGM-TIR, according to embodiments herein.
Figure 6A:
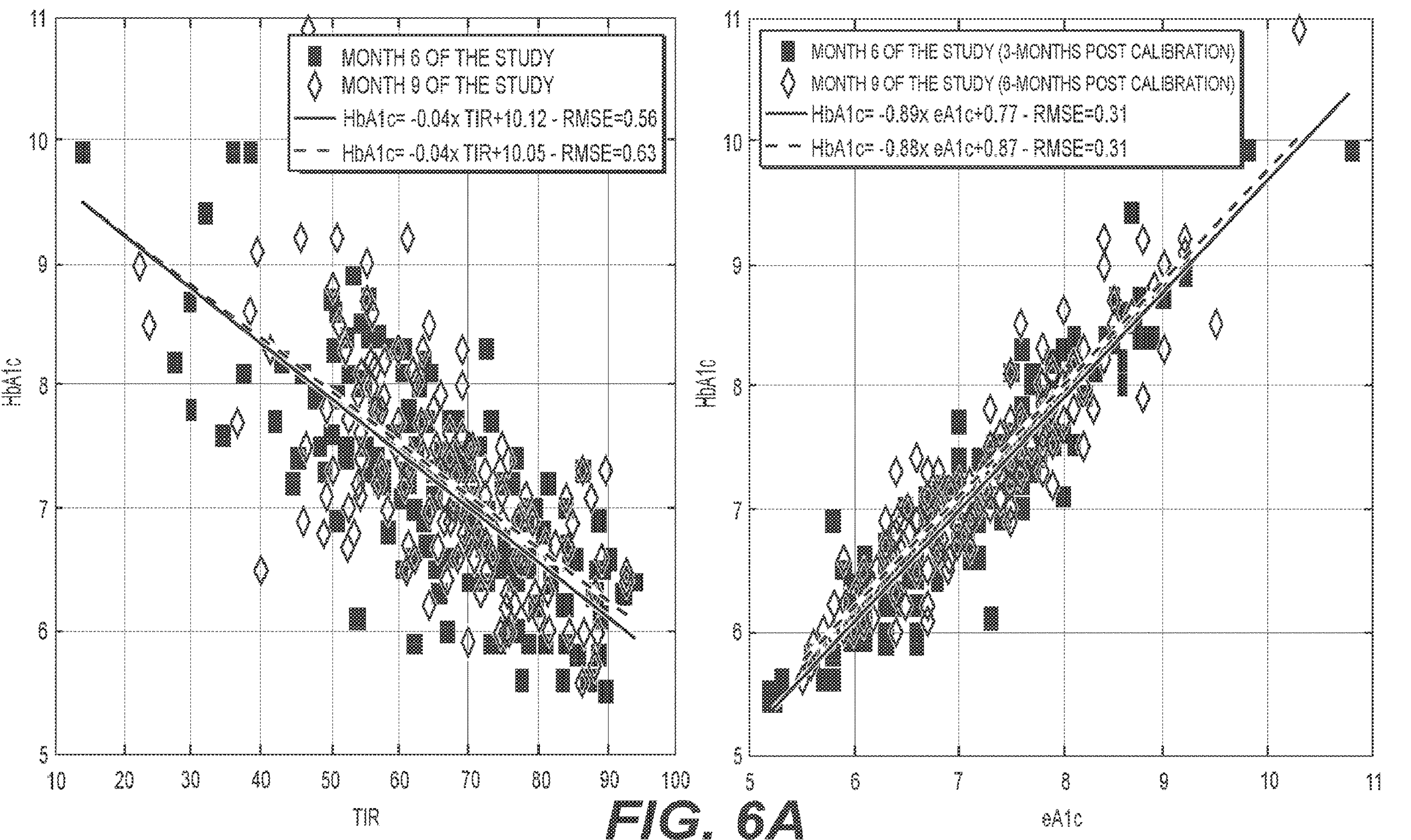
FIG. 6A illustrates comparison between CGM-TIR and eA1c, relative to laboratory HbA1c, with respect to embodiments herein.

The correlation (R) between TIR (computed from all the CGM data collected before a respective HbA1c measurement) and HbA1c at months 6 and 9 of the study were −0.75 and −0.66, corresponding to a coefficient of determination ($R^2$) of 0.56 and 0.44, respectively. By deploying the eA1c DM, the correlation between eA1c and HbA1c increased to 0.93 at month 6 (i.e., 3-month post-calibration) and remained stable at 0.93 at month 9 (i.e., 6-month post-calibration); this corresponded to an $R^2$ of 0.87 at month 6 and 0.86 at month 9. If correlated with TIR, eA1c showed results similar to HbA1c (yielding R=−0.77 at month 6 and R=−0.65 at month 9). That is, relative discordance remains substantially unchanged when eA1c is measured. Said otherwise, eA1c values remain in line with any of a correlation coefficient R and coefficient of determination $R^2$, so as to demonstrate, subsequent to individualization of the eA1c DM, low mean absolute difference (MAD) and mean absolute relative difference (MARD) when measured at month 6 and month 9. The correlation analysis is summarized in FIG. 6A and a summary of eA1c DM performance is presented in Table 2 below.

TABLE 2

PERFORMANCE OF THE A1c ESTIMATION ALORITHIM AFTER CALIBRATION WITH SINGLE LABORATORY HEMOGLOBIN A1c MEASUREMENT

| | Estimation of month 6 HbA1c (3-month postcalibration) | Estimation of month 9 HbA1c (6-month postcalibration) |
|---|---|---|
| Pearson's correlation coefficient | 0.93 | 0.93 |
| MAD | 0.25% | 0.24% |
| MARD | 3.5% | 3.4% |
| Percentage of eA1c assessments within 5% of laboratory HbA1c | 78.0% | 75.2% |
| Percentage of eA1c assessments within 10% of laboratory HbA1c | 97.6% | 96.3% |
| Percentage of eA1c assessments within 15% of laboratory HbA1c | 98.8% | 100% |

eA1c, estimated A1c; HbA1c, hemoglobin A1c; MAD, mean absolute difference; MARD, mean absolute relative difference.

Figure 7:
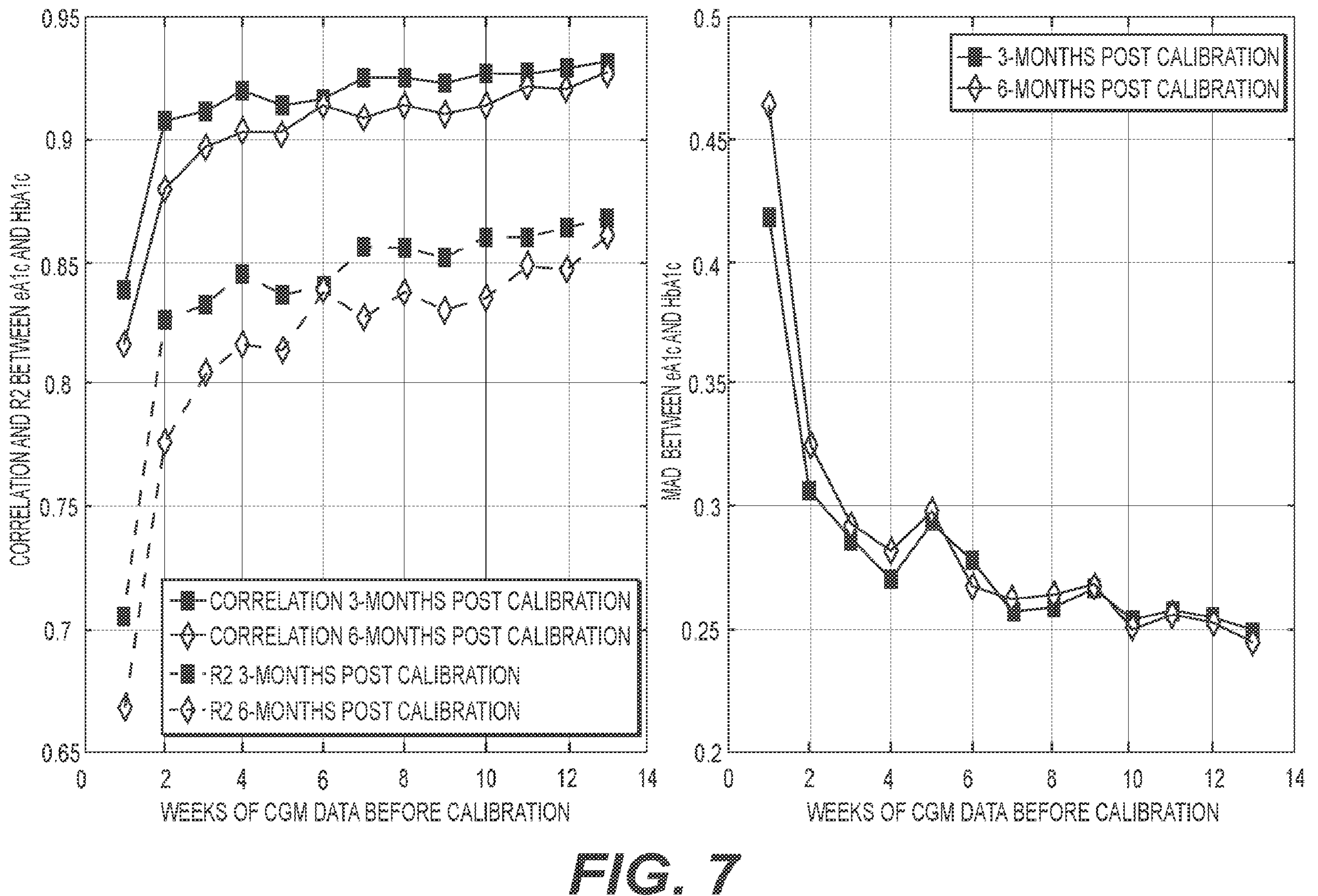
FIG. 7 illustrates the impact of a duration of a CGM run-in period with respect to measurement of eA1c accuracy, according to embodiments herein.

The impact of the duration of the CGM run-in period on eA1c accuracy is shown in FIG. 7. As visible, both the correlation between laboratory HbA1c and eA1c and their MAD stabilize and reach optimal values at about 2 to 3 weeks prior to calibration of the eA1c DM according to the patient-specific parameter γ.

Laboratory HbA1c has long been considered the best available measure to gauge the long-term quality of diabetes management and determine the success of therapy adjustments. However, the rapid progress made in the past two decades with CGM technology enables today a more reliable measurement of glucose levels across the glucose range, and thereby a better assessment of overall glycemic control. Herein, we demonstrate that HbA1c and CGM-TIR are different representations of the same underlying process of glycemic fluctuation; however, whereas CGM-TIR is a direct reflection of BG measurements, HbA1c is perturbed by each individual's rates of hemoglobin glycation and red blood cell clearance.

Reconciling laboratory HbA1c with CGM-based metrics of glycemic control is timely and has become more relevant as CGM daily profiles are increasingly deployed for clinical diabetes management. Among the various indicators designed to quantify glycemic control from CGM traces,[42] TIR is one of the core metrics that has been endorsed by a panel of expert clinicians and researchers convened at the 2017 International Conference on Advanced Technologies and Treatments for Diabetes to provide guidelines regarding the clinical use of CGM.[17] Two years later, a second panel agreed that "time in ranges"—a composite metric, including TIR, time below target range (TBR), and time above target range (TAR)—is an indicator of glycemic control that provides more actionable information than merely HbA1c alone,[18] and TIR or HbA1c should be complemented by measurements of exposure to hypoglycemia to allow a proper management of T1D.

Thus, we have introduced eA1c as a mediator between TIR and laboratory HbA1c, which accounts for daily BG fluctuations as reflected by CGM-TIR and individual glycation rates assessed through calibration of the eA1c DM based on a single laboratory HbA1c for each person. As has been discussed, the eA1c DM relies on a population model to convert daily CGM-TIR assessments to HbA1c units, and allows for an individualization of the model by a one-time calibration with a single laboratory HbA1c value. This fine-tuning provides high flexibility to the eA1c DM so as to enable it to fit patient-specific systematic deviations of laboratory HbA1c from average BG, therefore accommodating interindividual variation in laboratory HbA1c values and minimizing discrepancy between measured and CGM-TIR HbA1c values, i.e., eA1c values. Upon calibration, the eA1c DM has been demonstrated to provide accurate estimates of laboratory HbA1c for up to 6 months post-calibration and perhaps even longer thereafter, suggesting that effects of individual perturbations of laboratory HbA1c not related to glycemic exposure are stable over time and captured well by the calibration procedure (see FIG. 6A; Table 2).

Furthermore, based on the conducted model testing, 2 to 3 weeks of CGM data appear to be sufficient to allow for accurate calibration of the model (see FIG. 7).

The analysis hereinabove demonstrates the mismatch between laboratory HbA1c and CGM-derived measures of average glycemia, and strongly suggests that CGM-TIR may provide all of the information carried by HbA1c that pertains to the assessment of quality of glycemic control and effect of diabetes therapy. Through deployment, the eA1c DM may transform CGM-TIR into laboratory HbA1c units; thus, a well-defined mathematical relationship may be provided to enable quantitative evaluation. Because this relationship relies on calibration with laboratory HbA1c and can be traced back to laboratory HbA1c values, the use of the term "estimated A1c," or eA1c, is appropriate in this context. As will be appreciated from the discussion herein, eA1c represents a metric that adjusts a CGM-based assessment of glycemic control to account for individual glycation rates that are specific to each person, offering a multifactorial representation of BG fluctuation as well as biological factors that are independent from BG levels. In other words, eA1c represents an accurate estimate of what laboratory HbA1c can be expected to be, whereas the heretofore discussed GMI provides a representation of what HbA1c should be, if it was driven exclusively by glycemic state in the absence of individual glycation confounds.

Figure 8:
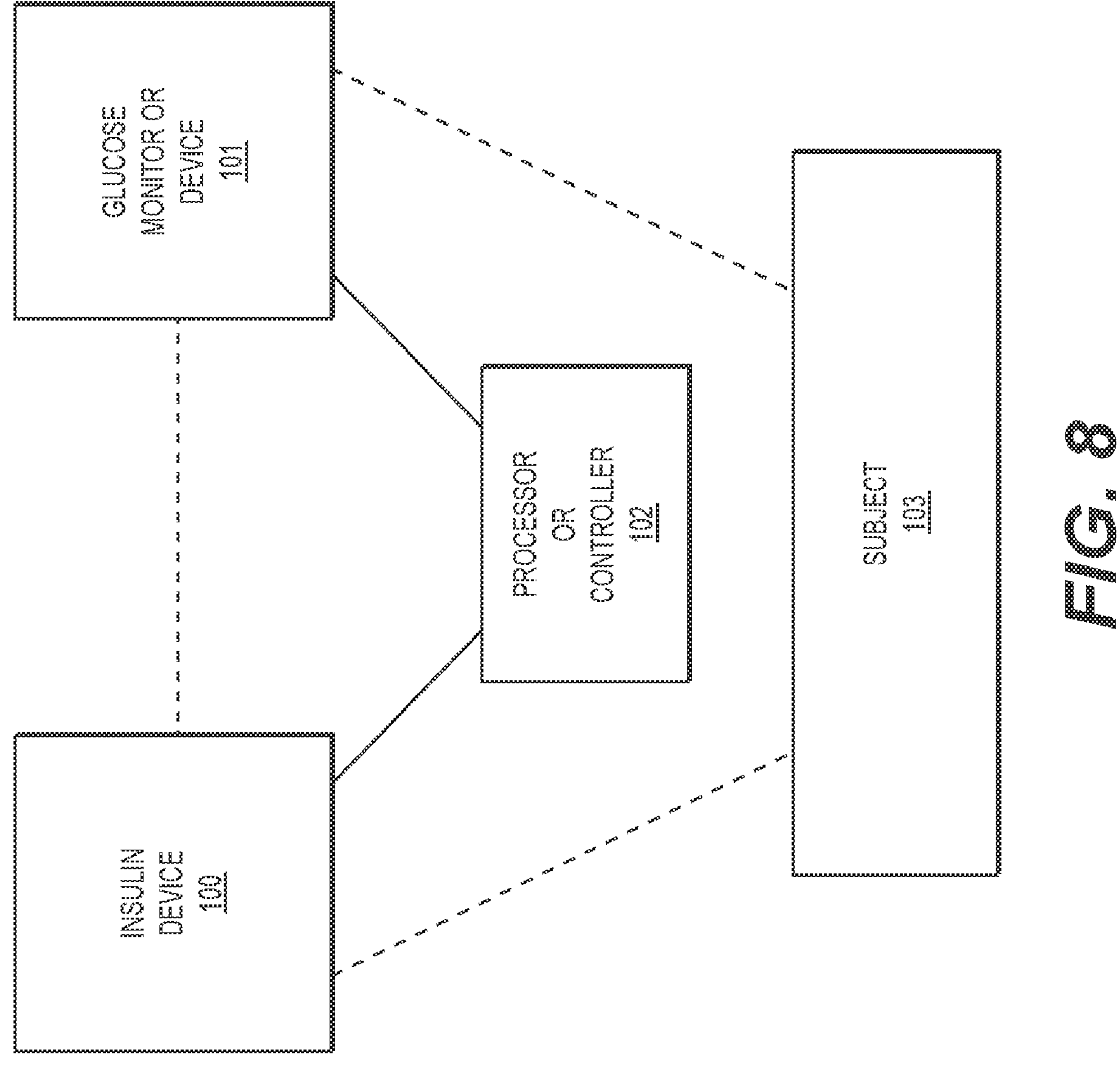
FIG. 8 illustrates a high level block diagram of the eA1c dynamical model (eA1c DM) environment according to embodiments herein.

Referring to FIG. 8, there is shown a high level functional block diagram of an environment enabling implementation of the eA1C DM according to embodiments herein.

As shown, a processor or controller 102 may be configured to implement the eA1C DM discussed above and to communicate with or within a CGM 101 (such as a DEXCOM G6), and optionally with an insulin device 100 enabled to deliver insulin. The glucose monitor or device 101 may communicate with a subject 103 to monitor glucose levels thereof. The processor or controller 102 may be configured to include all necessary hardware and/or software necessary to perform the required instructions to achieve the aforementioned tasks. Optionally, the insulin device 100 may communicate with the subject 103 to deliver insulin thereto. The glucose monitor 101 and the insulin device 100 may be implemented as separate devices or as a single device in combination. The processor 102 may be implemented locally in the glucose monitor 101, the insulin device 100, or as a standalone device (or in any combination of two or more of the glucose monitor, insulin device, or a standalone device). The processor 102 may be located remotely, such that the eA1C DM may be operated according to a telemedicine device.

Figure 9A:
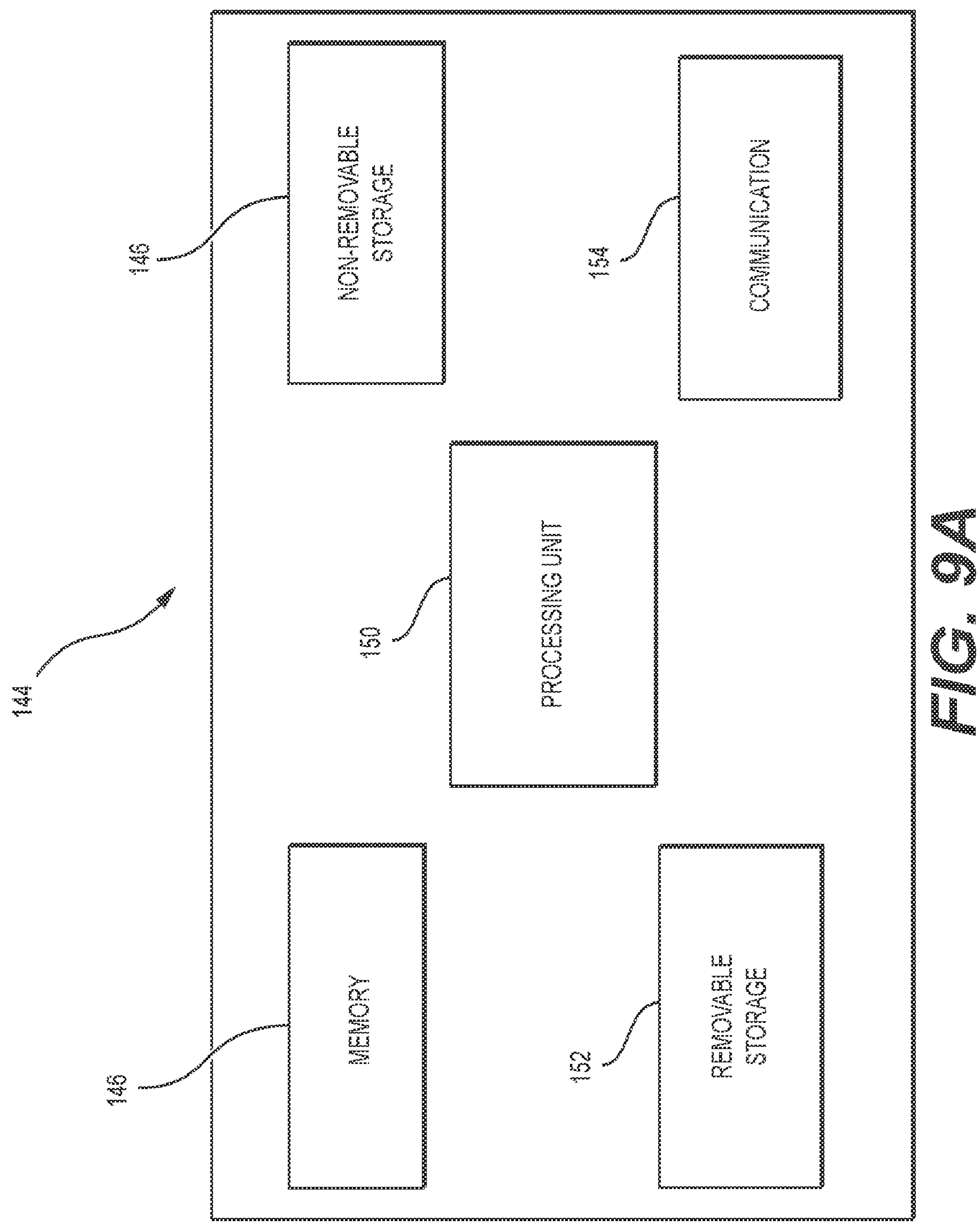
FIG. 9A illustrates an exemplary computing device which may implement the eA1c DM.

Referring to FIG. 9A, a computing device 144 may implement the eA1C DM and may typically include at least one processing unit 150 and memory 146. Depending on the exact configuration and type of computing device, memory 146 may be volatile (such as RAM), non-volatile (such as ROM, flash memory, etc.) or some combination of the two.

Additionally, computing device 144 may also have other features and/or functionality. For example, the device could also include additional removable and/or non-removable storage including, but not limited to, magnetic or optical disks or tape, as well as writable electrical storage media. Such additional storage may be represented as removable storage 152 and non-removable storage 148. Computer storage media may include volatile and nonvolatile, removable and non-removable media implemented in any method or technology for storage of information such as computer readable instructions, data structures, program modules or other data. The memory, the removable storage and the non-removable storage may comprise examples of computer storage media. Computer storage media may include, but not be limited to, RAM, ROM, EEPROM, flash memory or other memory technology CDROM, digital versatile disks (DVD) or other optical storage, magnetic cassettes, magnetic tape, magnetic disk storage or other magnetic storage devices, or any other medium which can be used to store the desired information and which can accessed by the device. Any such computer storage media may be part of, or used in conjunction with, one or more components implementing the eA1C DM.

The computer device 144 may also contain one or more communications connections 154 that allow the device to communicate with other devices (e.g. other computing devices). The communications connections may carry information in a communication media. Communication media may typically embody computer readable instructions, data structures, program modules or other data in a modulated data signal, such as a carrier wave or other transport mechanism and includes any information delivery media. The term "modulated data signal" may include a signal that has one or more of its characteristics set or changed in such a manner as to encode, execute, or process information in the signal. By way of example, and not limitation, communication medium may include wired media such as a wired network or direct-wired connection, and wireless media such as radio, RF, infrared and other wireless media. As discussed above, the term computer readable media as used herein may include both storage media and communication media.

Figure 9B:
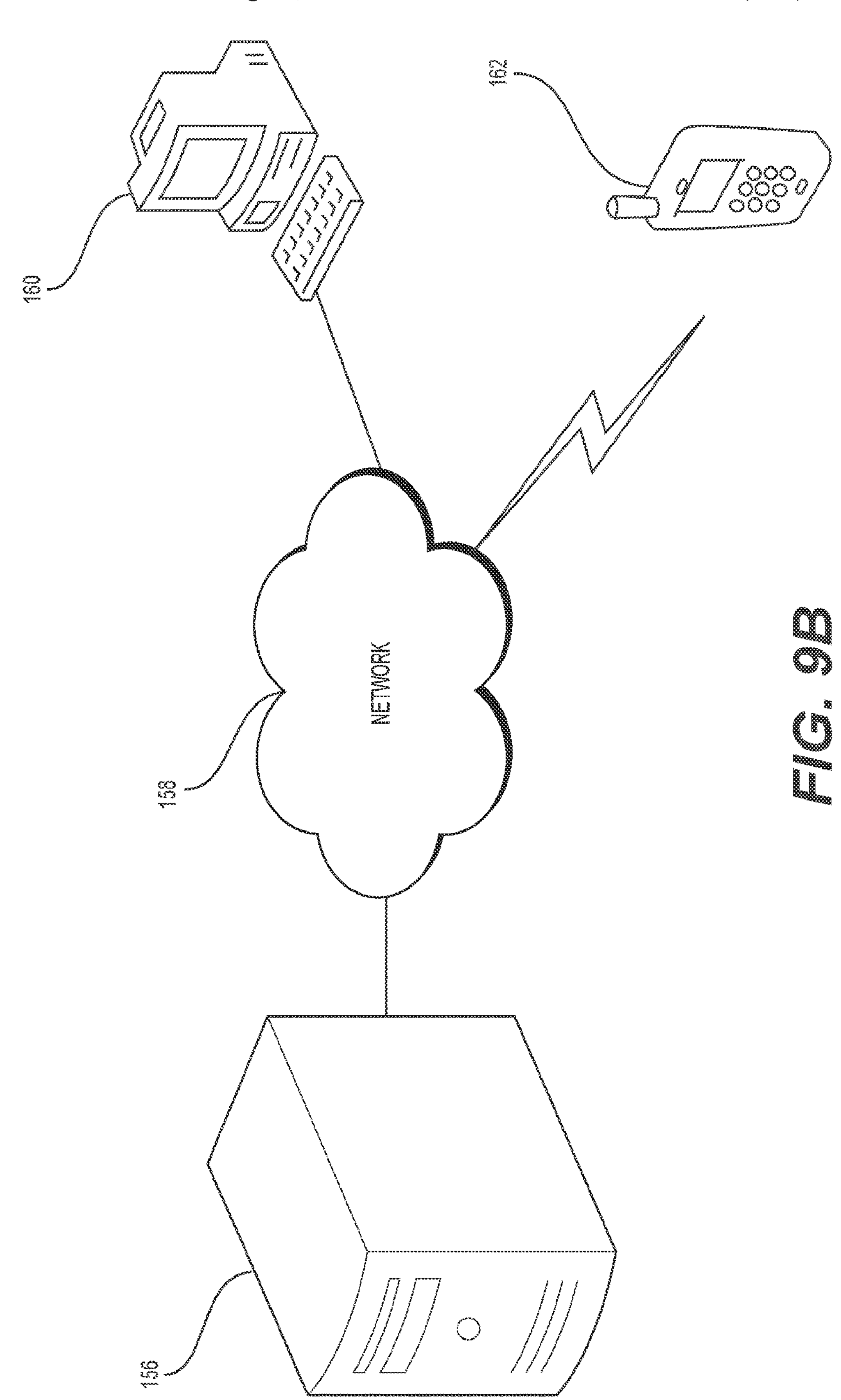
FIG. 9B illustrates a network system which may implement and/or be used in the implementation of the eA1c DM.

In addition to a stand-alone computing machine, embodiments herein may also be implemented on a network system comprising a plurality of computing devices that may in communication via a network, such as a network with an infrastructure or an ad hoc network. The network connection may include wired connections or wireless connections. For example, FIG. 9B illustrates a network system in which embodiments herein may be implemented. In this example, the network system may comprise a computer 156 (e.g., a network server), network connection means 158 (e.g., wired and/or wireless connections), a computer terminal 160, and a PDA (e.g., a smartphone) 162 (or other handheld or portable device, such as a cell phone, laptop computer, tablet computer, GPS receiver, mp3 player, handheld video player, pocket projector, etc. or other handheld devices (or non-portable devices) with combinations of such features). In an embodiment, it should be appreciated that the module listed as 156 may implement a CGM. In an embodiment, it should be appreciated that the module listed as 156 may be a glucose monitor device, an artificial pancreas, and/or an insulin device. Any of the components shown or discussed with FIG. 9B may be multiple in number. Embodiments herein may be implemented in anyone of the aforementioned devices. For example, execution of the instructions or other desired processing may be performed on the same computing device that is anyone of 156, 160, and 162. Alternatively, an embodiment may be performed on different computing devices of the network system. For example, certain desired or required processing or execution may be performed on one of the computing devices of the network (e.g. server 156 and/or a CGM), whereas other processing and execution of the instruction can be performed at another computing device (e.g., terminal 160) of the network system, or vice versa. In fact, certain processing or execution may be performed at one computing device (e.g. server 156 or CGM 101); and the other processing or execution of the instructions may be performed at different computing devices that may or may not be networked. For example, such certain processing may be performed at terminal 160, while the other processing or instructions may be passed to device 162 where the instructions may be executed. This scenario may be of particular value especially when the PDA 162 device, for example, accesses the network through computer terminal 160 (or an access point in an ad hoc network). For another example, software comprising the instructions may be executed, encoded or processed according to one or more embodiments herein. The processed, encoded or executed instructions may then be distributed to customers in the form of a storage media (e.g. disk) or electronic copy.

FIG. 10 illustrates a block diagram that of a system 130 including a computer system 140 and the associated Internet 11 connection upon which an embodiment may be implemented. Such configuration may typically be used for computers (i.e., hosts) connected to the Internet 11 and executing software on a server or a client (or a combination thereof). A source computer such as laptop, an ultimate destination computer and relay servers, for example, as well as any computer or processor described herein, may use the computer system configuration and the Internet connection shown in FIG. 9. The system 140 may take the form of a portable electronic device such as a notebook/laptop computer, a media player (e.g., a MP3 based or video player), a cellular phone, a Personal Digital Assistant (PDA), a CGM, an AP, an insulin delivery device, an image processing device (e.g., a digital camera or video recorder), and/or any other handheld computing devices, or a combination of any of these devices. Note that while FIG. 9 illustrates various components of a computer system, it is not intended to represent any particular architecture or manner of interconnecting the components; as such, details of such interconnection are omitted. It will also be appreciated that network computers, handheld computers, cell phones and other data processing systems which have fewer components or perhaps more components may also be used. The computer system of FIG. 9 may, for example, be an Apple Macintosh computer or Power Book, or an IBM compatible PC. Computer system 140 may include a bus 137, an interconnect, or other communication mechanism for communicating information, and a processor 138, commonly in the form of an integrated circuit, coupled with bus 137 for processing information and for executing the computer executable instructions. Computer system 140 may also include a main memory 134, such as a Random Access Memory (RAM) or other dynamic storage device, coupled to bus 137 for storing information and instructions to be executed by processor 138.

Main memory 134 also may be used for storing temporary variables or other intermediate information during execution of instructions to be executed by processor 138. Computer system 140 may further include a Read Only Memory (ROM) 136 (or other non-volatile memory) or other static storage device coupled to bus 137 for storing static information and instructions for processing by processor 138. A storage device 135, such as a magnetic disk or optical disk, a hard disk drive for reading from and writing to a hard disk, a magnetic disk drive for reading from and writing to a magnetic disk, and/or an optical disk drive (such as a DVD) for reading from and writing to a removable optical disk, may be coupled to bus 137 for storing information and instructions. The hard disk drive, magnetic disk drive, and optical disk drive may be connected to the system bus by a hard disk drive interface, a magnetic disk drive interface, and an optical disk drive interface, respectively. The drives and their associated computer readable media may provide non-volatile storage of computer readable instructions, data structures, program modules and other data for the general purpose computing devices. Typically, computer system 140 may include an Operating System (OS) stored in a non-volatile storage for managing the computer resources and may provide the applications and programs with an access to the computer resources and interfaces. An operating system commonly processes system data and user input, and responds by allocating and managing tasks and internal system resources, such as controlling and allocating memory, prioritizing system requests, controlling input and output devices, facilitating networking and managing files. Non-limiting examples of OSs may include Microsoft Windows, Mac OS X, and Linux.

The term "processor" may include any integrated circuit or other electronic device (or collection of such electronic devices) capable of performing an operation on at least one instruction including, without limitation, Reduced Instruction Set Core (RISC) processors, CISC microprocessors, Microcontroller Units (MCUs), CISC-based Central Processing Units (CPUs), and Digital Signal Processors (DSPs). The hardware of such devices may be integrated onto a single substrate (e.g., a silicon "die"), or may be distributed among two or more substrates. Furthermore, various functional aspects of the processor may be implemented solely as software or firmware associated with the processor.

Computer system 140 may be coupled via bus 137 to a display 131, such as a Cathode Ray Tube (CRT), a Liquid Crystal Display (LCD), a flat screen monitor, a touch screen monitor or similar means for displaying text and graphical data to a user. The display may be connected via a video adapter for supporting the display. The display may allow a user to view, enter, and/or edit information that may be relevant to the operation of the system. An input device 132, including alphanumeric and other keys, may be coupled to bus 137 for communicating information and command selections to processor 138. Another type of user input device may include cursor control 133, such as a mouse, a trackball, or cursor direction keys for communicating direction information and command selections to processor 138, and for controlling cursor movement on display 131. Such an input device may include two degrees of freedom in two axes, a first axis (e.g., x) and a second axis (e.g., y), that may allow the device to specify positions in a plane.

The computer system 140 may be used for implementing the methods and techniques described herein. According to an embodiment, those methods and techniques may be performed by computer system 140 in response to processor 138 executing one or more sequences of one or more instructions contained in main memory 134. Such instructions may be read into main memory 134 from another computer readable medium, such as storage device 135. Execution of the sequences of instructions contained in main memory 134 may cause processor 138 to perform the process steps described herein. In alternative embodiments, hard-wired circuitry may be used in place of or in combination with software instructions to implement the arrangement. Thus, embodiments of the invention may not be limited to any specific combination of hardware circuitry and software.

The term "computer readable medium" (or "machine readable medium") as used herein is an extensible term that refers to any medium or any memory, that participates in providing instructions to a processor, (such as processor 138), for execution, or any mechanism for storing or transmitting information in a form readable by a machine (e.g., a computer). Such a medium may store computer-executable instructions to be executed by a processing element and/or control logic, and data which may be manipulated by a processing element and/or control logic, and may take many forms, including but not limited to, non-volatile medium, volatile medium, and transmission medium. Transmission media may include coaxial cables, copper wire and fiber optics, including the wires that comprise bus 137. Transmission media may also take the form of acoustic or light waves, such as those generated during radio-wave and infrared data communications, or other form of propagated signals (e.g., carrier waves, infrared signals, digital signals, etc.). Common forms of computer readable media include, for example, a floppy disk, a flexible disk, hard disk, magnetic tape, or any other magnetic medium, a CD-ROM, any other optical medium, punch-cards, paper-tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 138 for execution. For example, the instructions may initially be carried on a magnetic disk of a remote computer. The remote computer may load the instructions into its dynamic memory and send the instructions over a telephone line using a modem. A modem local to computer system 140 may receive the data on the telephone line and use an infra-red transmitter to convert the data to an infra-red signal. An infra-red detector may receive the data carried in the infra-red signal, and appropriate circuitry may place the data on bus 137. Bus 137 may carry the data to main memory 134, from which processor 138 may retrieve and execute the instructions. The instructions received by main memory 134 may optionally be stored on storage device 135 either before or after execution by processor 138.

Computer system 140 may also include a communication interface 141 coupled to bus 137. Communication interface 141 may provide a two-way data communication coupling to a network link 139 that may be connected to a local network 111. For example, communication interface 141 may be an Integrated Services Digital Network (ISDN) card or a modem to provide a data communication connection to a corresponding type of telephone line. As another non-limiting example, communication interface 141 may be a local area network (LAN) card to provide a data communication connection to a compatible LAN. For example, Ethernet based connection based on IEEE802.3 standard may be used such as 10/100 BaseT, 1000 BaseT (gigabit Ethernet), 10 gigabit Ethernet (10 GE or 10 GbE or 10 GigE per IEEE Std 802.3ae-2002 as standard), 40 Gigabit Ethernet (40 GbE), or 100 Gigabit Ethernet (100 GbE as per Ethernet standard IEEE P802.3ba), as described in Cisco Systems, Inc. Publication number 1-587005-001-3 (6/99), "Internetworking Technologies Handbook", Chapter 7: "Ethernet Technologies", pages 7-1 to 7-38, which is incorporated in its entirety for all purposes as if fully set forth herein. In such a case, the communication interface 141 may typically include a LAN transceiver or a modem, such as Standard Microsystems Corporation (SMSC) LAN91C111 10/100 Ethernet transceiver described in the Standard Microsystems Corporation (SMSC) data-sheet "LAN91C111 10/100 Non-PCI Ethernet Single Chip MAC+PHY" Data-Sheet, Rev. 15 (02-20-04), which is incorporated in its entirety for all purposes as if fully set forth herein.

Wireless links may also be implemented. In any such implementation, communication interface 141 may send and receive electrical, electromagnetic or optical signals that may carry digital data streams representing various types of information.

Network link 139 may typically provide data communication through one or more networks to other data devices. For example, network link 139 may provide a connection through local network 111 to a host computer or to data equipment operated by an Internet Service Provider (ISP) 142. ISP 142, in turn, may provide data communication services through the world wide packet data communication network Internet 11. Local network 111 and Internet 11 may both use electrical, electromagnetic or optical signals that carry digital data streams. The signals through the various networks and the signals on the network link 139 and through the communication interface 141, which carry the digital data to and from computer system 140, are exemplary forms of carrier waves transporting the information.

A received code may be executed by processor 138 as it is received, and/or stored in storage device 135, or other non-volatile storage for later execution. In this manner, computer system 140 may obtain application code in the form of a carrier wave.

In view of the above, calculation of eA1c through use of the eA1C DM discussed herein may be readily applicable into devices with (for example) limited processing power, such as glucose, insulin, and AP devices, and may be implemented and utilized with the related processors, networks, computer systems, internet, and components and functions according to the schemes disclosed herein.

Figure 11:
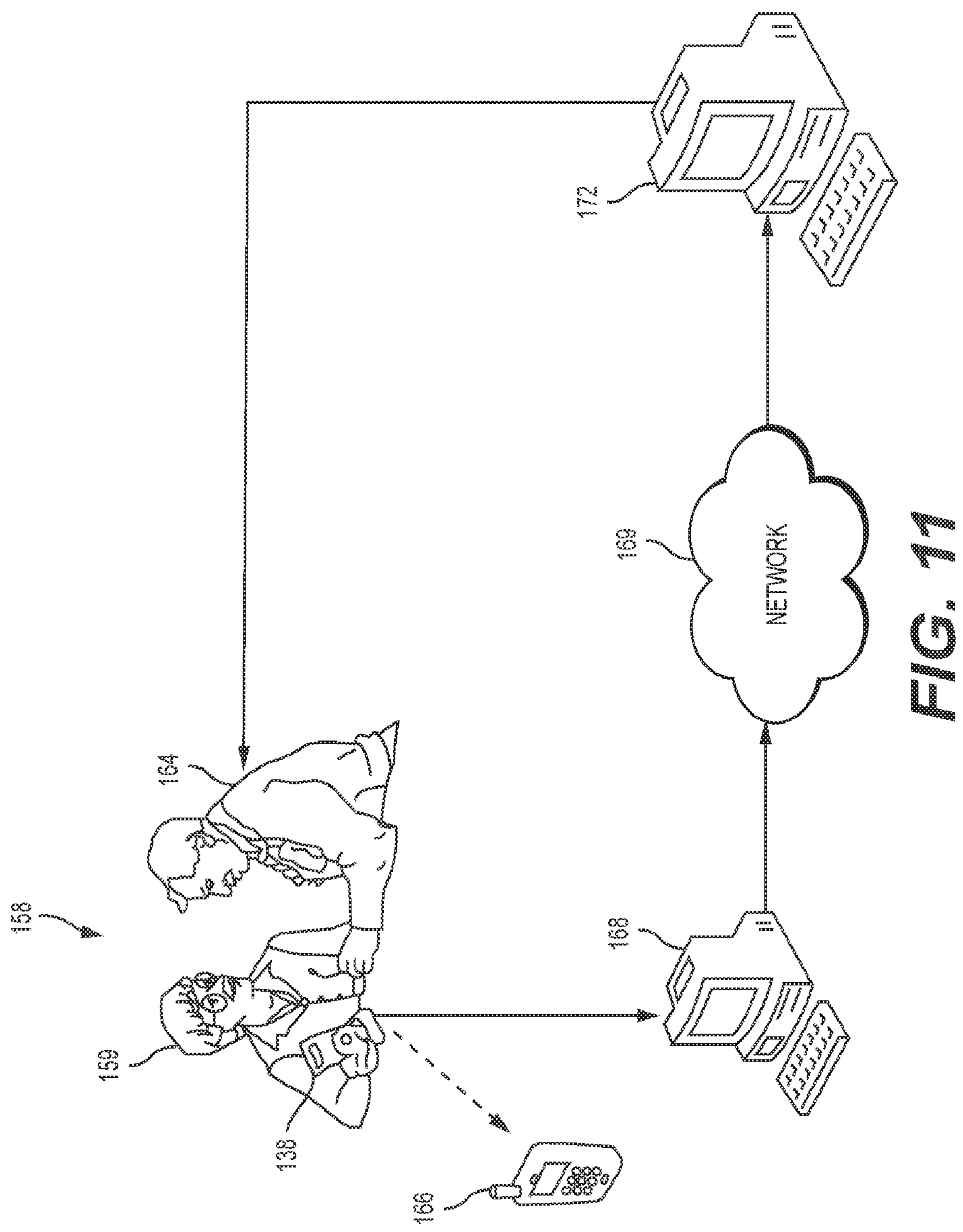
FIG. 11 illustrates a system which may implement and/or be used in the implementation of the eA1c DM in accordance with one or more of a clinical setting and a connection to the Internet.

Referring to FIG. 11, there is shown an exemplary system for implementing embodiments herein. In an embodiment, the CGM, or the insulin device may be implemented by a subject (or patient) locally at home or at another desired location. However, in an alternative embodiment, one or more of the above may be implemented in a clinical setting. For instance, referring to FIG. 11, a clinical setup 158 may provide a place for doctors (e.g., 164) or clinician/assistant to diagnose patients (e.g., 159) with diseases related with glucose, and related diseases and conditions. A CGM 10 may be used to monitor and/or test the glucose levels of the patient—as a standalone device. It should be appreciated that while only one CGM 10 is shown in the figure, the system may include other components. The system or component, such as the CGM 10, may be affixed to the patient or in communication with the patient as desired or required. For example, the system or combination of components thereof—including a CGM 10 (or other related devices or systems such as a controller, and/or an AP, an insulin pump, or any other desired or required devices or components)—may be in contact, communication or affixed to the patient through tape or tubing (or other medical instruments or components) or may be in communication through wired or wireless connections. Such monitoring and/or testing may be short term (e.g., a clinical visit) or long term (e.g., a clinical stay). The CGM 10 may output results that may be used by the doctor (, clinician or assistant) for appropriate actions, such as insulin injection or food feeding for the patient, or other appropriate actions or modeling. Alternatively, the CGM 10 may output results that may be delivered to computer terminal 168 for instant or future analyses. The delivery may be through cable or wireless or any other suitable medium. The CGM 10 output from the patient may also be delivered to a portable device, such as PDA 166. The CGM 10 output may also be delivered to a glucose monitoring center 172 for processing and/or analyzing. Such delivery can be accomplished in many ways, such as network connection 170, which may be wired or wireless.

In addition to the CGM 10 output, errors, parameters for accuracy improvements, and any accuracy related information may be delivered, such as to computer 168, and/or glucose monitoring center 172 for performing error analyses. Doing so may provide centralized monitoring of accuracy, modeling and/or accuracy enhancement for glucose centers, relative to assuring a reliable dependence upon glucose sensors.

Examples of the invention may also be implemented in a standalone computing device associated with the target glucose monitoring device. An exemplary computing device (or portions thereof) in which examples of the invention may be implemented is schematically illustrated in FIG. 8A.

Figure 12:
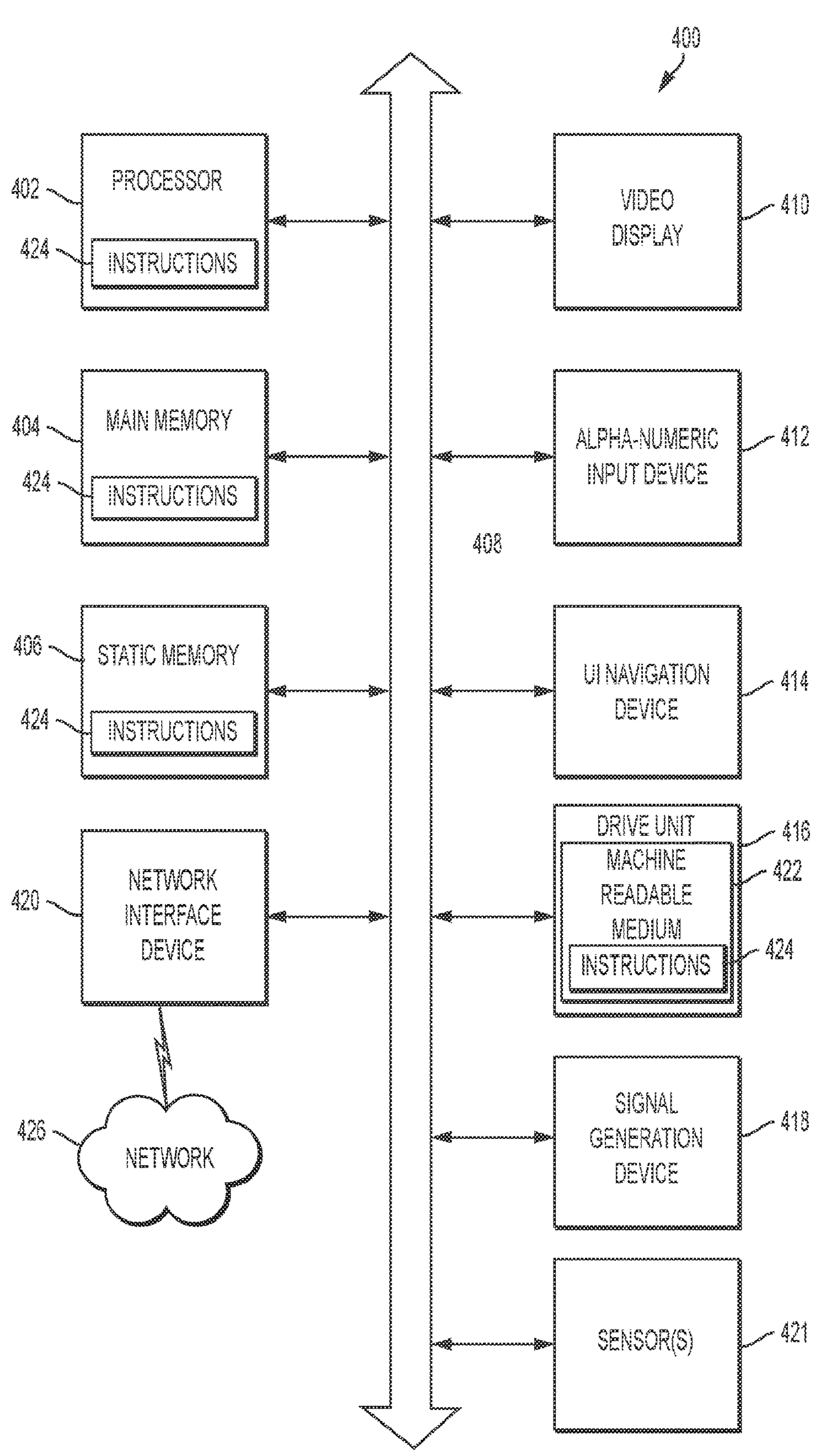
FIG. 12 illustrates an exemplary architecture embodying the eA1c DM.

FIG. 12 provides a block diagram illustrating an exemplary machine upon which one or more aspects of embodiments, including methods thereof, herein may be implemented.

Machine 400 may include logic, one or more components, and circuits (e.g., modules). Circuits may be tangible entities configured to perform certain operations. In an example, such circuits may be arranged (e.g., internally or with respect to external entities such as other circuits) in a specified manner. In an example, one or more computer systems (e.g., a standalone, client or server computer system) or one or more hardware processors (processors) may be configured with or by software (e.g., instructions, an application portion, or an application) as a circuit that operates to perform certain operations as described herein. In an example, the software may reside (1) on a non-transitory machine readable medium or (2) in a transmission signal. In an example, the software, when executed by the underlying hardware of the circuit, may cause the circuit to perform the certain operations.

In an example, a circuit may be implemented mechanically or electronically. For example, a circuit may comprise dedicated circuitry or logic that may be specifically configured to perform one or more techniques such as are discussed above, including a special-purpose processor, a field programmable gate array (FPGA) or an application-specific integrated circuit (ASIC). In an example, a circuit may comprise programmable logic (e.g., circuitry, as encompassed within a general-purpose processor or other programmable processor) that may be temporarily configured (e.g., by software) to perform certain operations. It will be appreciated that the decision to implement a circuit mechanically (e.g., in dedicated and permanently configured circuitry), or in temporarily configured circuitry (e.g., configured by software) may be driven by cost and time considerations.

Accordingly, the term "circuit" may be understood to encompass a tangible entity, whether physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time. For example, where the circuits comprise a general-purpose processor configured via software, the general-purpose processor may be configured as respective different circuits at different times. Software may accordingly configure a processor, for example, to constitute a particular circuit at one instance of time and to constitute a different circuit at a different instance of time.

In an example, circuits may provide information to, and receive information from, other circuits. In this example, the circuits may be regarded as being communicatively coupled to one or more other circuits. Where multiple of such circuits exist contemporaneously, communications may be achieved through signal transmission (e.g., over appropriate circuits and buses) that connect the circuits. In embodiments in which multiple circuits are configured or instantiated at different times, communications between such circuits may be achieved, for example, through the storage and retrieval of information in memory structures to which the multiple circuits have access. For example, one circuit may perform an operation and store the output of that operation in a memory device to which it is communicatively coupled. A further circuit may then, at a later time, access the memory device to retrieve and process the stored output. In an example, circuits may be configured to initiate or receive communications with input or output devices and may operate on a collection of information.

The various operations of methods described herein may be performed, at least partially, by one or more processors that may temporarily configured (e.g., by software) or permanently configured to perform the relevant operations. Whether temporarily or permanently configured, such processors may constitute processor-implemented circuits that operate to perform one or more operations or functions. In an example, the circuits referred to herein may comprise processor-implemented circuits.

Similarly, the methods described herein may be at least partially processor-implemented. For example, at least some of the operations of a method may be performed by one or processors or processor-implemented circuits. The performance of certain of the operations may be distributed among the one or more processors, not only residing within a single machine, but deployed across a number of machines. In an example, the processor or processors may be located in a single location (e.g., within a home environment, an office environment or as a server farm), while in other examples the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., Application Program Interfaces (APIs)).

Example embodiments (e.g., apparatus, systems, or methods) may be implemented in digital electronic circuitry, in computer hardware, in firmware, in software, or in any combination thereof. Example embodiments may be implemented using a computer program product (e.g., a computer program, tangibly embodied in an information carrier or in a machine readable medium, for execution by, or to control the operation of, data processing apparatus such as a programmable processor, a computer, or multiple computers).

A computer program may be written in any form of programming language, including compiled or interpreted languages, and may be deployed in any form, including as a stand-alone program or as a software module, subroutine, or other unit suitable for use in a computing environment. A computer program may be deployed to be executed on one computer or on multiple computers at one site or distributed across multiple sites and interconnected by a communication network.

In an example, operations may be performed by one or more programmable processors executing a computer program to perform functions by operating on input data and generating output. Examples of method operations may also be performed by, and example apparatus can be implemented as, special purpose logic circuitry (e.g., a field programmable gate array (FPGA) or an application-specific integrated circuit (ASIC)).

The computing system or systems herein may include clients and servers. A client and server may generally be remote from each other and generally interact through a communication network. The relationship of client and server arises by virtue of computer programs running on the respective computers and having a client-server relationship to each other. In embodiments deploying a programmable computing system, it will be appreciated that both hardware and software architectures may be adapted, as appropriate. Specifically, it will be appreciated that whether to implement certain functionality in permanently configured hardware (e.g., an ASIC), in temporarily configured hardware (e.g., a combination of software and a programmable processor), or a combination of permanently and temporarily configured hardware may be a function of efficiency. Below are set out hardware (e.g., machine 400) and software architectures that may be implemented in or as example embodiments.

In an example, the machine 400 may operate as a standalone device or the machine 400 may be connected (e.g., networked) to other machines.

In a networked deployment, the machine 400 may operate in the capacity of either a server or a client machine in server-client network environments. In an example, machine 400 may act as a peer machine in peer-to-peer (or other distributed) network environments. The machine 400 may be a personal computer (PC), a tablet PC, a set-top box (STB), a Personal Digital Assistant (PDA), a mobile telephone, a web appliance, a network router, switch or bridge, or any machine capable of executing instructions (sequential or otherwise) specifying actions to be taken (e.g., performed) by the machine 400. Further, while only a single machine 400 is illustrated, the term "machine" shall also be taken to include any collection of machines that individually or jointly execute a set (or multiple sets) of instructions to perform any one or more of the embodiments discussed herein.

Example machine (e.g., computer system) 400 may include a processor 402 (e.g., a central processing unit (CPU), a graphics processing unit (GPU) or both), a main memory 404 and a static memory 406, some or all of which may communicate with each other via a bus 408. The machine 400 may further include a display unit 410, an alphanumeric input device 412 (e.g., a keyboard), and a user interface (UI) navigation device 411 (e.g., a mouse). In an example, the display unit 410, input device 412 and UI navigation device 414 may be a touch screen display. The machine 400 may additionally include a storage device (e.g., drive unit) 416, a signal generation device 418 (e.g., a speaker), a network interface device 420, and one or more sensors 421, such as a global positioning system (GPS) sensor, compass, accelerometer, or other sensor. The storage device 416 may include a machine readable medium 422 on which is stored one or more sets of data structures or instructions 424 (e.g., software) embodying or utilized by any one or more of the methodologies or functions described herein. The instructions 424 may also reside, completely or at least partially, within the main memory 404, within static memory 406, or within the processor 402 during execution thereof by the machine 400. In an example, one or any combination of the processor 402, the main memory 404, the static memory 406, or the storage device 416 may constitute machine readable media.

While the machine readable medium 422 is illustrated as a single medium, the term "machine readable medium" may include a single medium or multiple media (e.g., a centralized or distributed database, and/or associated caches and servers) that may be configured to store the one or more instructions 424. The term "machine readable medium" may also be taken to include any tangible medium that may be capable of storing, encoding, or carrying instructions for execution by the machine and that cause the machine to perform any one or more of the embodiments of the present disclosure or that may be capable of storing, encoding or carrying data structures utilized by or associated with such instructions. The term "machine readable medium" may accordingly be understood to include, but not be limited to, solid-state memories, and optical and magnetic media. Specific examples of machine readable media may include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 424 may further be transmitted or received over a communications network 426 using a transmission medium via the network interface device 420 utilizing any one of a number of transfer protocols (e.g., frame relay, IP, TCP, UDP, HTTP, etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., IEEE 802.11 standards family known as Wi-Fi®, IEEE 802.16 standards family known as WiMax®), peer-to-peer (P2P) networks, among others. The term "transmission medium" may include any intangible medium that may be capable of storing, encoding or carrying instructions for execution by the machine, and includes digital or analog communications signals or other intangible medium to facilitate communication of such software.

REFERENCES

The following patents, applications and publications as listed below and throughout this document are hereby incorporated by reference in their entirety herein, and which are not admitted to be prior art with respect to embodiments herein by inclusion in this section. Where applicable, citations herein refer to one or more of the documents below.

1. Diabetes Control and Complications Trial Research Group. The effect of intensive treatment of diabetes on the development and progression of long-term complications in insulin-dependent diabetes mellitus. N Engl J Med 1993; 329:977-986.
2. Diabetes Control and Complications Trial Research Group. The relationship of glycemic exposure (HbA1c) to the risk of development and progression of retinopathy in the Diabetes Control and Complications Trial. Diabetes 1995; 44:968-983.
3. Welsh K J, Kirkman M S, Sacks D B. Role of glycated proteins in the diagnosis and management of diabetes: research gaps and future directions. Diabetes Care 2016; 39:1299-1306.
4. Hirsch I B. Glycemic variability: it's not just about A1C anymore! Diabetes Technol Ther 2005; 7:780-783.
5. Brownlee M, Hirsch I B. Glycemic variability: a hemoglobin A1c-independent risk factor for diabetic complications. JAMA 2006; 295:1707-1708.

6. Hirsch I B. Glycemic variability and diabetes complications: does it matter? Of course it does! Diabetes Care 2015; 38:1610-1614.
7. Cohen R M, Franco R S, Khera P K, et al. Red cell life span heterogeneity in hematologically normal people is sufficient to alter HbA1c. Blood 2008; 112:4284-4291.
8. Malka R, Nathan D M, Higgins J M. Mechanistic modeling of hemoglobin glycation and red blood cell kinetics enables personalized diabetes monitoring. Sci Transl Med 2016; 8: 359ra130.
9. Hempe J M, Gomez R, McCarter R J, Chalew S A. High and low hemoglobin glycation phenotypes in type 1 diabetes: a challenge for interpretation of glycemic control. J Diabetes Complicat 2002; 16:313-320.
10. Kirk J K, D'Agostino R B, Bell R A, et al. Disparities in HbA1c levels between African-American and non-Hispanic white adults with diabetes: a meta-analysis. Diabetes Care 2006; 29:2130-2136.
11. Herman W H, Ma Y, Uwaifo G, et al. Differences in A1C by race and ethnicity among patients with impaired glucose tolerance in the Diabetes Prevention Program. Diabetes Care 2007; 30:2453-2457.
12. Kamps J L, Hempe J M, Chalew S A. Racial disparity in A1C independent of mean blood glucose in children with type 1 diabetes. Diabetes Care 2010; 33:1025-1027.
13. Herman W H. Are there clinical implications of racial differences in HbA1c? Yes, to not consider can do great harm! Diabetes Care 2016; 39:1458-1461.
14. Selvin E. Are there clinical implications of racial differences in HbA1c? A Difference, to be a difference, must make a difference. Diabetes Care 2016; 39:1462-1467.
15. Bergenstal R M, Gal R L, Connor C G, et al. Racial differences in the relationship of glucose concentrations and hemoglobin A1c levels. Ann Intern Med 2017; 167:95-102.
16. Beck R W, Connor C G, Mullen D M, et al. The fallacy of average: how using HbA1c alone to assess glycemic control can be misleading. Diabetes Care 2017; 40:994-999.
17. Danne T, Nimri R, Battelino T, et al. International consensus on use of continuous glucose monitoring. Diabetes Care 2017; 40:1631-1640.
18. Battelino T, Danne T, Bergenstal R M, et al. Clinical targets for continuous glucose monitoring data interpretation: recommendations from the international consensus on time in range. Diabetes Care 2019; 42:1593-1603.
19. Bry L, Chen P C, Sacks D B. Effects of hemoglobin variants and chemically modified derivatives on assays for glycohemoglobin. Clin Chem 2001; 47:153-163.
20. National Institute of Diabetes and Digestive and Kidney Diseases. Sickle cell trait and other hemoglobinopathies and diabetes (for providers) [Internet]. https://www.niddk.nih.gov/health-information/professionals/clinical-tools-patient-management/diabetes/sickle-cell-trait-hemoglobinopathies-diabetes (accessed Apr. 7, 2020).
21. Ford E S, Cowie C C, Li C, et al. Iron-deficiency anemia, non-iron-deficiency anemia and HbA1c among adults in the US. J Diabetes 2011; 3:67-73.
22. Nielsen L R, Ekbom P, Damm P, et al. HbA1c levels are significantly lower in early and late pregnancy. Diabetes Care 2004; 27:1200-1201.
23. Nathan D M, Kuenen J, Borg R, et al. Translating the A1C assay into estimated average glucose values. Diabetes Care 2008; 31:1473-1478.
24. Kovatchev B P, Flacke F, Sieber J, Breton M D. Accuracy and robustness of dynamical tracking of average glycemia (A1c) to provide real-time estimation of hemoglobin A1c using routine self-monitored blood glucose data. Diabetes Technol Ther 2014; 16:303-309.
25. Kovatchev B P, Breton M D. Hemoglobin A1c and self-monitored average glucose: validation of the dynamical tracking eA1c algorithm in type 1 diabetes. J Diabetes Sci Technol 2015; 10:330-335.
26. Xu Y, Dunn T C, Ajjan R A. A kinetic model for glucose levels and hemoglobin A1c provides a novel tool for individualized diabetes management. J Diabetes Sci Technol 2020 Jan. 8; 1932296819897613.
27. Bergenstal R M, Beck R W, Close K L, et al. Glucose management indicator (GMI): a new term for estimating A1C from continuous glucose monitoring. Diabetes Care 2018; 41:2275-2280.
28. Leelarathna L, Beck R W, Bergenstal R M, et al. Glucose management indicator (GMI): insights and validation using Guardian 3 and Navigator 2 sensor data. Diabetes Care 2019; 42:e60-e61.
29. Soros A A, Chalew S A, McCarter R J, et al. Hemoglobin glycation index: a robust measure of hemoglobin A1c bias in pediatric type 1 diabetes patients. Pediatr Diabetes 2010; 11:455-461.
30. McCarter R J, Hempe J M, Gomez R, Chalew S A. Biological variation in HbA1c predicts risk of retinopathy and nephropathy in type 1 diabetes. Diabetes Care 2004; 27:1259-1264.
31. Diabetes Research in Children Network (DirecNet) Study Group. Relationship of A1C to glucose concentrations in children with type 1 diabetes: assessments by high-frequency glucose determinations by sensors. Diabetes Care 2008; 31:381-385.
32. Lachin J M, Genuth S, Nathan D M, Rutledge B N. The hemoglobin glycation index is not an independent predictor of the risk of microvascular complications in the Diabetes Control and Complications Trial. Diabetes 2007; 56:1913-1921.
33. Hempe J M, Liu S, Myers L, et al. The hemoglobin glycation index identifies subpopulations with harms or benefits from intensive treatment in the ACCORD trial. Diabetes Care 2015; 38:1067-1074.
34. Wright L A-C, Hirsch I B. Metrics beyond hemoglobin A1C in diabetes management: time in range, hypoglycemia, and other parameters. Diabetes Technol Ther 2017; 19(S2):S16-S26.
35. Beck R W, Bergenstal R M, Cheng P, et al. The relationships between time in range, hyperglycemia metrics, and HbA1c. J Diabetes Sci Technol 2019; 13:614-626.
36. Beck R W, Bergenstal R M, Riddlesworth T D, et al. Vali-dation of time in range as an outcome measure for diabetes clinical trials. Diabetes Care 2019; 42:400-405.
37. Lu J, Ma X, Zhou J, et al. Association of time in range, as assessed by continuous glucose monitoring, with diabetic retinopathy in type 2 diabetes. Diabetes Care 2018; 41: 2370-2376.
38. Lu J, Ma X, Shen Y, et al. Time in range is associated with carotid intima-media thickness in type 2 diabetes. Diabetes Technol Ther 2020; 22:72-78.

39. Moscardó V, Herrero P, Reddy M, et al. Assessment of glucose control metrics by discriminant ratio. Diabetes Technol Ther 2020. doi: 10.1089/dia.2019.0415.
40. Kovatchev B, Anderson S M, Raghinaru D, et al. Randomized controlled trial of mobile closed-loop control. Diabetes Care 2020; 43:607-615.
41. Brown S A, Kovatchev B P, Raghinaru D, et al. Six-month randomized, multicenter trial of closed-loop control in type 1 diabetes. N Engl J Med 2019; 381: 1707-1717.
42. Kovatchev B P. Metrics for glycaemic control—from HbA1c to continuous glucose monitoring. Nat Rev Endocrinol 2017; 13:425-436.
43. Rodbard D. Glucose time in range, time above range, and time below range depend on mean or median glucose or HbA1c, glucose coefficient of variation, and shape of the glucose distribution. Diabetes Technol Ther 2020. doi: 10.1089/dia.2019.0440.
44. Fabris C, Heinemann L, Beck R W, Cobelli C, and Kovatchev B. Estimation of Hemoglobin A1c From Continuous Glucose Monitoring Data in Individuals With Type 1 Diabetes: Is Time in Range All We Need? Diabetes Technol Ther. 2020 doi: 10.1089/dia.2020.0236. PMID: 32459124.

In summary, embodiments herein present a manner of estimating laboratory HbA1c, as a value of eA1c based on daily CGM-TIR data and which is adjusted in accordance with a sole laboratory HbA1c value. In particular, the sole laboratory HbA1c value may correspond to a first interval in time preceding a second interval in time for which the value of eA1c may be obtained. Specifically, the first interval may correspond to a period of 3 months of CGM-TIR and the second interval may correspond to a period of 3 months subsequent to the first interval. Further intervals may be relatively compared, as well, such that, relative to the 6 month period exemplified, the first interval may occur at month 6 and the second interval may occur at month 9.

Although the present embodiments have been described in detail, those skilled in the art will understand that various changes, substitutions, variations, enhancements, nuances, gradations, lesser forms, alterations, revisions, improvements and knock-offs of the embodiments disclosed herein may be made without departing from the spirit and scope of the embodiments in their broadest form.

What is claimed is:

1. A processor-implemented method for providing a real-time estimation of laboratory glycosylated hemoglobin (HbA1c) of a patient at one or more predetermined intervals, as a value of estimated A1c (eA1c) based on continuous glucose monitoring (CGM)-derived time in target range (TIR) (CGM-TIR) for said patient, said method comprising:
clinically measuring one or more values of laboratory HbA1c from respective specimens being collected from said patient and respectively corresponding to said one or more predetermined intervals; and
calculating said value of eA1c for a respective one of said one or more predetermined intervals in accordance with one or more processors configured to
(a) receive daily CGM-TIR data of said patient for said one or more predetermined intervals,
(b) transform said received daily CGM-TIR data into units corresponding to said one or more values of laboratory HbA1c at said one or more predetermined intervals,
(c) determine a glycation rate of said patient based on only a respective one of said one or more values of laboratory HbA1c of said patient, and
(d) adjust said transformed CGM-TIR data based on said determined glycation rate to determine an amount of insulin infusion to said patient according to said calculating of said value of eA1c.

2. The method according to claim 1, wherein:
said received CGM-TIR data is fed to a predetermined glycation equation to obtain said transformation of said received CGM-TIR data.

3. The method of claim 2, wherein:
said predetermined glycation equation comprises $$\frac{\partial eA1c}{\partial t} = \frac{-1}{\tau}\left(eA1c - \gamma \cdot f_{CGM-TIR}\right),$$

where
eA1c is estimated A1c,
∂eA1c/∂t is a derivate of said eA1c,
$\tau$ is a clearance rate of said eA1c,
$f_{CGM-TIR}$ is a linear function of said received daily CGM-TIR data for a target range thereof of 70-180 mg/dL, in which $f_{CGM-TIR}$=m·CGM-TIR+q, and $\tau$, m, and q are population based parameter values which are determined for a given value of HbA1c measured outside of said predetermined intervals and generic to said patient, and
$\gamma$ is a parameter value specific to said patient for yielding said glycation rate to modulate glycation gain to allow a lower or a higher value of eA1c for a same value of $f_{CGM-TIR}$.

4. The method according to claim 3, wherein:
$\gamma$ is determined for an individual one of said one or more predetermined intervals preceding another of said one or more predetermined intervals.

5. The method according to claim 4, wherein:
$\gamma$ is determined based on said respective one of said one or more values of laboratory HbA1c, wherein said respective value corresponds to said individual one of said one or more predetermined intervals preceding another of said one or more predetermined intervals.

6. The method according to claim 5, further comprising:
comparing said value of eA1c to one of said one or more values of laboratory HbA1c, for a respectively corresponding one of said one or more predetermined intervals, to determine a relative difference therebetween.

7. A system for providing a real-time estimation of laboratory glycosylated hemoglobin (HbA1c) of a patient at one or more predetermined intervals, as a value of estimated A1c (eA1c) based on continuous glucose monitoring (CGM)-derived time in target range (TIR) (CGM-TIR) for said patient, comprising:
a processor; and
a processor-readable memory including processor-executable instructions for:
clinically measuring one or more values of laboratory HbA1c from respective specimens being collected from said patient and respectively corresponding to said one or more predetermined intervals; and
calculating said value of eA1c for a respective one of said one or more predetermined intervals by
(a) receiving daily CGM-TIR data of said patient for said one or more predetermined intervals,
(b) transforming said received daily CGM-TIR data into units corresponding to said one or more values of laboratory HbA1c at said one or more predetermined intervals, (c) determining a glycation rate of said patient based on only a respective one of said one or more values of laboratory HbA1c of said patient, and (d) adjusting said transformed CGM-TIR data based on said determined glycation rate to determine an amount of insulin infusion to said patient according to said calculating of said value of eA1c.

8. The system according to claim 7, wherein:

said received CGM-TIR data is fed to a predetermined glycation equation to obtain said transformation of said received CGM-TIR data.

9. The system of claim 8, wherein:

said predetermined glycation equation comprises $$\frac{\partial eA1c}{\partial t} = \frac{-1}{\tau}\left(eA1c - \gamma \cdot f_{CGM-TIR}\right),$$

where eA1c is estimated A1c, $\partial eA1c/\partial t$ is a derivate of said eA1c, $\tau$ is a clearance rate of said eA1c, $f_{CGM-TIR}$ is a linear function of said received daily CGM-TIR data for a target range thereof of 70-180 mg/dL, in which $f_{CGM-TIR}$=m·CGM-TIR+q, and $\tau$, m, and q are population based parameter values which are determined for a given value of HbA1c measured outside of said predetermined intervals and generic to said patient, and $\gamma$ is a parameter value specific to said patient for yielding said glycation rate to modulate glycation gain to allow a lower or a higher value of eA1c for a same value of $f_{CGM-TIR}$.

10. The system according to claim 9, wherein:

$\gamma$ is determined for an individual one of said one or more predetermined intervals preceding another of said one or more predetermined intervals.

11. The system according to claim 10, wherein:

$\gamma$ is determined based on said respective one of said one or more values of laboratory HbA1c, wherein said respective value corresponds to said individual one of said one or more predetermined intervals preceding another of said one or more predetermined intervals.

12. The system according to claim 11, further comprising:

comparing said value of eA1c to one of said one or more values of laboratory HbA1c, for a respectively corresponding one of said one or more predetermined intervals, to determine a relative difference therebetween.

13. A non-transient computer-readable medium having stored thereon computer-executable instructions for providing a real-time estimation of laboratory glycosylated hemoglobin (HbA1c) of a patient at one or more predetermined intervals, as a value of estimated A1c (eA1c) based on continuous glucose monitoring (CGM)-derived time in target range (TIR) (CGM-TIR) for said patient, said instructions comprising instructions causing a computer to:

clinically measure one or more values of laboratory HbA1c from respective specimens being collected from said patient and respectively corresponding to said one or more predetermined intervals; and calculate said value of eA1c for a respective one of said one or more predetermined intervals by (a) receiving daily CGM-TIR data of said patient for said one or more predetermined intervals, (b) transforming said received daily CGM-TIR data into units corresponding to said one or more values of laboratory HbA1c at said one or more predetermined intervals, (c) determining a glycation rate of said patient based on only a respective one of said one or more values of laboratory HbA1c of said patient, and (d) adjusting said transformed CGM-TIR data based on said determined glycation rate to determine an amount of insulin infusion to said patient according to said calculating of said value of eA1c.

14. The computer-readable medium according to claim 13, wherein:

said received CGM-TIR data is fed to a predetermined glycation equation to obtain said transformation of said received CGM-TIR data.

15. The computer-readable medium according to claim 14, wherein:

said predetermined glycation equation comprises $$\frac{\partial eA1c}{\partial t} = \frac{-1}{\tau}\left(eA1c - \gamma \cdot f_{CGM-TIR}\right),$$

where eA1c is estimated A1c, $\partial eA1c/\partial t$ is a derivate of said eA1c, $\tau$ is a clearance rate of said eA1c, $f_{CGM-TIR}$ is a linear function of said received daily CGM-TIR data for a target range thereof of 70-180 mg/dL, in which $f_{CGM-TIR}$=m·CGM-TIR+q, and $\tau$, m, and q are population based parameter values which are determined for a given value of HbA1c measured outside of said predetermined intervals and generic to said patient, and $\gamma$ is a parameter value specific to said patient for yielding said glycation rate to modulate glycation gain to allow a lower or a higher value of eA1c for a same value of $f_{CGM-TIR}$.

16. The computer-readable medium according to claim 15, wherein:

$\gamma$ is determined for an individual one of said one or more predetermined intervals preceding another of said one or more predetermined intervals.

17. The computer-readable medium according to claim 16, wherein:

$\gamma$ is determined based on said respective one of said one or more values of laboratory HbA1c, wherein said respective value corresponds to said individual one of said one or more predetermined intervals preceding another of said one or more predetermined intervals.

18. The computer-readable medium according to claim 17, further including instructions for causing a computer to:

compare said value of eA1c to one of said one or more values of laboratory HbA1c, for a respectively corresponding one of said one or more predetermined intervals, to determine a relative difference therebetween.

* * * * *